(12) United States Patent
Sutter et al.

(10) Patent No.: US 8,452,670 B2
(45) Date of Patent: May 28, 2013

(54) COMPUTER-ENABLED METHOD AND SYSTEM FOR FACILITATING VETERINARY PHARMACEUTICAL AND OTHER ANIMAL-RELATED PRODUCT CATALOG CUSTOMIZATION

(75) Inventors: Donald C. Sutter, Tulsa, OK (US); Kurt D. Green, Portland, OR (US); Thomas A. Friar, Portland, OR (US); Andrew J. Bane, Portland, OR (US)

(73) Assignee: Strategic Pharmaceutical Solutions, Inc., Portland, OR (US)

( * ) Notice: Subject to any disclaimer, the term of this patent is extended or adjusted under 35 U.S.C. 154(b) by 242 days.

(21) Appl. No.: 13/022,842

(22) Filed: Feb. 8, 2011

(65) Prior Publication Data
US 2012/0203671 A1 Aug. 9, 2012

(51) Int. Cl.
*G06Q 30/00* (2012.01)
*G06Q 10/00* (2012.01)
*G06F 17/30* (2006.01)

(52) U.S. Cl.
USPC ............. 705/27.1; 705/28; 707/781; 707/784

(58) Field of Classification Search
USPC ............................ 705/27.1, 28; 707/781, 784
See application file for complete search history.

(56) References Cited

U.S. PATENT DOCUMENTS

| | | | |
|---|---|---|---|
| 6,978,273 B1 * | 12/2005 | Bonneau et al. | 1/1 |
| 2004/0030649 A1 * | 2/2004 | Nelson et al. | 705/44 |
| 2007/0260476 A1 * | 11/2007 | Smolen et al. | 705/1 |
| 2010/0161345 A1 * | 6/2010 | Cain et al. | 705/2 |

OTHER PUBLICATIONS

Author: www.petcarerx.com; Title of the Article: Discount pet meds, pet medications and pet medicines—PetCareRx pet pharmacy; Title of the item: www.petcarerx.com/pcrx/default.aspx; Date: copyright notice date on webpage 1998-2010; p. 1-2; Publisher: www.petcarerx.com; City and/or Country: World Wide—Internet.
Author: www.petmedsonline.org; Title of the Article: Pet Health Products for Dogs; Title of the item: www.petmedsonline.org/pet-health-meds-for-dogs.html; Date: copyright notice date on webpage 2006-2011; p. 1-2; Publisher: www.petmedsonline.org; City and/or Country: World Wide—Internet.
Author: www.1800petmeds.com; Title of Article: 1800PetMeds.com Catalog; Title of the item: http://www.1800petmeds.com/catalog/catalogdetail.jsp?id=14&pg=1; Date: copyright notice date on webpage 2011; p. 1-2; Publisher: www.1800petmeds.com; City and/or Country: World Wide—Internet.
Author: www.drsfostersmith.com; Title of the Article: Pet Supplies: Products for your pet selected by our veterinarians; Title of the item: http://www.drsfostersmith.com/general.cfm?gid=1116; Date: copyright notice date on webpage 1997-2011; p. 1-3; Publisher: www.drsfostersmith.com; City and or Country: World Wide—Internet.

* cited by examiner

*Primary Examiner* — Nicholas D Rosen
(74) *Attorney, Agent, or Firm* — Howard Russell

(57) ABSTRACT

A computer-enabled method for efficiently displaying automatically generated, customizable views of a master product item catalog of veterinary pharmaceutical and other animal-related product item records provided by a centralized pharmacy to a large number of veterinarians, veterinary hospitals and customers, the views comprising administrator views, hospital staff views and user views, the views being selectively excludable and modifiable by each hospital administrator via an exception-type customization and hospital manageable database, access to which is provided for each hospital on the central pharmacy's server, each hospital being enabled to provide customers and staff of the hospital access to its customized catalog via point-of-sale and e-commerce points of access over the Internet or other network.

17 Claims, 20 Drawing Sheets

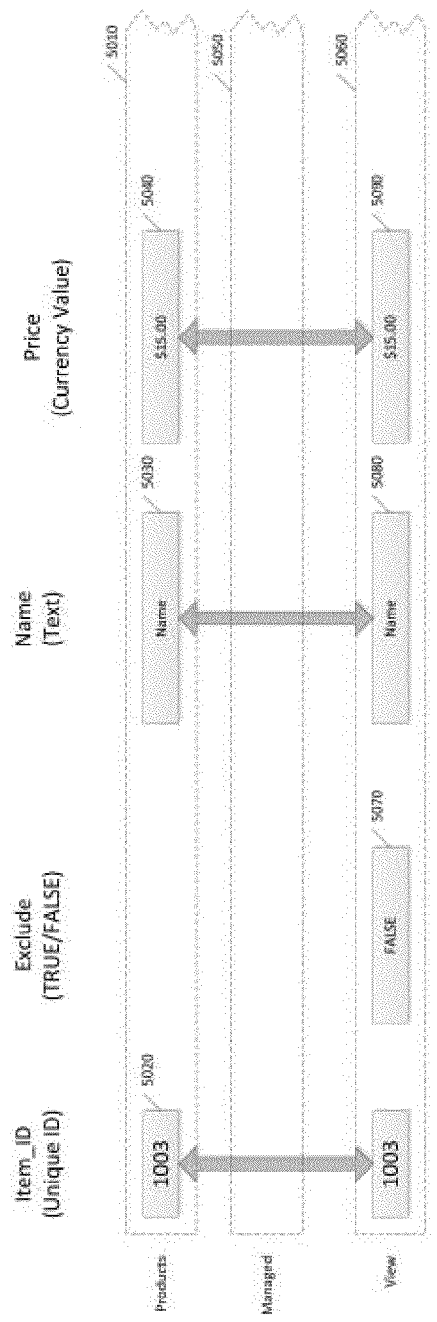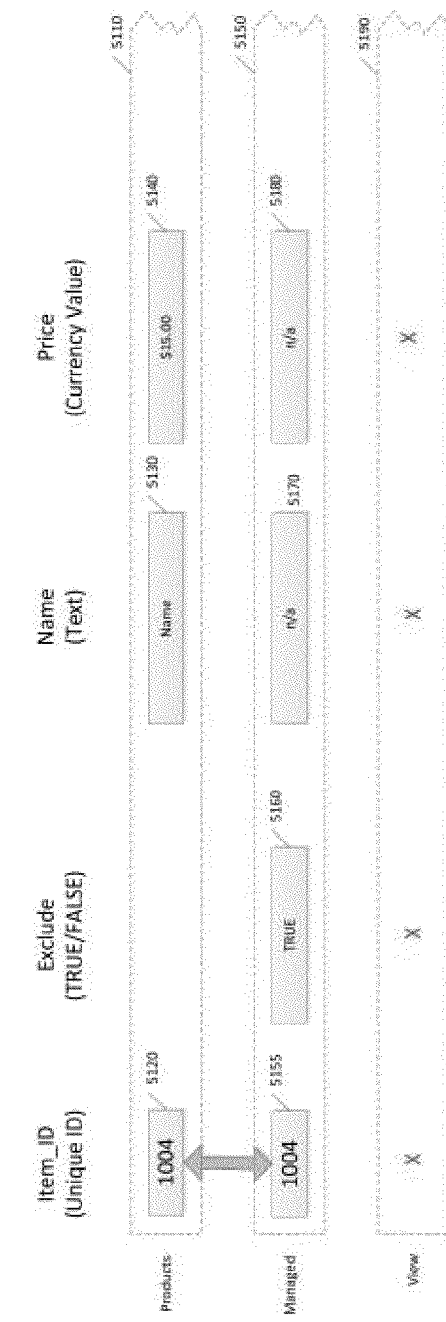

COMPUTER-ENABLED METHOD AND SYSTEM FOR FACILITATING VETERINARY PHARMACEUTICAL AND OTHER ANIMAL-RELATED PRODUCT CATALOG CUSTOMIZATION

BACKGROUND OF THE INVENTION

The present invention relates in general to product marketing, product selection, and product catalog entry customization relating to the sale of veterinary pharmaceuticals and other animal-related products, and in particular the present invention relates to a computer-enabled, integrated, e-commerce method and system for facilitating the dynamic building and providing of a customized catalog of available products and related information to veterinarians relating to the sale of veterinary pharmaceuticals and other animal-related products.

FIG. 1 illustrates the traditional and often repeated scenario of an animal owner that has brought an animal, such as a pet, to a veterinarian at an animal hospital, including any animal treatment facility or location where a licensed veterinarian is authorized to do business, for treatment of a condition as shown at 10 to respond to illness of the animal or improve the animal's health. Once the veterinarian has examined the animal, and based on observations and medical experience, the veterinarian communicates a verbal treatment plan as shown at 12 and issues a written prescription to the owner as shown at 14. FIG. 1 also illustrates that compliance to fulfill the script at 16 and to administer treatment to the animal at 20 in accordance with the treatment plan has been almost exclusively dependent upon the animal owner.

However, this traditional method of treating animals with animal-related products has been subject to the primary shortfall of non-compliance of administering the recommended treatment to the animal as illustrated at 26, 28. Largely, such noncompliance has resulted from inherent delay and the inconvenience placed upon the owner to return to the veterinarian to renew prescriptions, to hand-carry prescriptions to the local pharmacy, wait to have them filled, and to remember to administer the treatment as prescribed to the animal according to the treatment plan. Thus, non-compliance may include any deviation from the treatment plan of the veterinarian, such as an owner's failure to renew the prescription, failure to refill the prescription and do so in a timely manner as shown at 22, or failure to administer the treatment and do so in a timely manner according to the treatment plan as shown at 26, 28. Since the animal has been mostly unable to indicate need for treatment, compliance has been left primarily to the owner in this traditional scenario, and diminished compliance has resulted.

In the case of treatments that have involved the administration of multiple doses of medicine or supplement on a periodic basis, for example weekly, in the past the owner has had the option of purchasing an initial quantity of medication or supplement sufficient for the entire anticipated treatment period, to be administered in multiple subsequent periodic installments at the sole remembering and initiative of the animal owner. Or, in the case of ongoing treatments over time, the animal owner might have been required in the past to return to the veterinary pharmacy for filling of subsequent installments of treatments prior to the owner's having administered such subsequent treatment to the animal. But as shown at 22 and 26, neither the return to the pharmacy, and as a result, nor the administration of the treatment occurred, illustrating noncompliance with the treatment plan.

It is distressing that there has been a very low compliance rate in the administration of pharmaceuticals to animals, documented as between 34-48 percent among customers of veterinary preventative medications, and 19% for therapeutic diets, as published in the 2003 AAHA study, *The Path to High-Quality Care: Practical Tips for Improving Compliance*.

Traditionally, pharmacy's within veterinary hospitals, and especially those within smaller animal treatment facilities or locations where only one or just a few licensed veterinarians have been authorized to do business, have struggled to profitably and effectively manage and dispense veterinary pharmaceuticals and animal supplements. This has been in part due to the lack of a system for effectively integrating animal pharmacies and animal care providers such as veterinarians and veterinary hospitals.

Since there is currently a very large number of supplement and pharmaceutical treatment options available for animals presenting a wide variety of disorders and conditions, it has been very difficult, if not impossible, for a veterinarian, or a small veterinary hospital, to have maintained in stock sufficient quantities of each of the many and varied medications available, without such supplies becoming stale, losing potency, or expiring. Further, the management of such inventory, even if possible, would be very cumbersome, labor intensive, and expensive. Since there is such a wide variety of pharmaceutical, over-the-counter and supplement treatment options for animals today, it has been very difficult for an in-hospital pharmacy to stay current on and keep all of the many products available in fresh supply. This problem has been exacerbated by the fact that, with some medications or products the number of animals for which the product may have been beneficially prescribed has been relatively small.

From an animal pharmacy's perspective, it has been difficult to integrate many disparate providers of animal care services with a standard product offering that is effectively managed, given the many different products available and the fact that the product list and pricing is constantly changing. Such difficulty has further acted to prevent involvement of individual veterinarians and animal hospitals in transactions involving the sale of veterinary pharmaceuticals and other animal-related products, since pharmacies have had only less effective means of marketing to and creating relationships with animal care providers. For example, prior methods of marketing animal pharmaceutical products to veterinarians has involved a system of advance sheets and traditional marketing literature provided to veterinarians and hospitals by drug manufacturers, together with drug sales representatives who have called on the veterinarians and hospitals.

Accordingly, it has been a challenge for veterinary hospitals and veterinarians to participate successfully in, and profit from the sale of, pharmaceutical and other animal-related products for treatment of animals seen at the veterinary hospital. And this, in turn, has negatively impacted the treatment of animals, since already low rates of compliance with veterinary treatment regimens overall are worsened where the veterinarian is not effectively involved, financially or otherwise, in the pharmaceutical and supplement dispensing and supplying process. This situation is complicated in the case of treatments that have involved the administration of multiple doses of medicine or supplement on a periodic basis, for example weekly, or daily for a period of time.

Prior non-computerized methods and systems of enabling, controlling and managing the processing, fulfilling, dispensing and handling of sales of animal-related products have not included a customizable, automated means of product offering, selection, billing, accounting and proceeds sharing capability to enable veterinarians and animal hospitals to effectively participate and profit from the sale directly to customers of the increasingly larger varieties of products available. As such, traditional prior art methods and systems of dispensing veterinary pharmaceuticals have not employed effective means for veterinarians and their staff to participate in the product sale transaction and thus more positively impact compliance of the animal owner in using the prescribed medication or supplement to support more effective treatment outcomes. Thus, in addition to the need for an effective and automated method of enabling customized product marketing, offerings and selection, as well as controlling sales and distribution of animal-related products, there has been needed an effective and automated method to include animal hospitals and veterinarians in the distribution of proceeds from sales of such products.

Prior attempts to address the basic limitations of manual ordering, fulfillment and dispensing of animal product systems, as with a typically customer-centric, centralized pharmacy accessible by the customer, or alternatively by the veterinarian, by telephone or the Internet, have not adequately involved the animal hospital, or veterinarian, in the process, either from a dispensing follow-up standpoint or from a financial standpoint. Thus, while such systems have enabled improvements, allowing greater ease for the animal owner to access the pharmacy via telephone or Internet, and hence there has been slightly less likelihood of delay in fulfilling prescriptions, these systems have not effectively incentivized participation of the animal hospital and thus have not adequately accounted for beneficial participation by the animal hospital in the transaction. And this ultimately has negatively impacted compliance with animal treatment plans.

Further, though with previously described methods and systems, sometimes a veterinarian has been able to call in, fax in, or email in a prescription directly to the central pharmacy for manual pickup by the customer, such solutions have lacked a coherent strategy and computerized system for marketing and offering both pharmaceutical and other animal-related products for selection by the animal care provider. Such a system is needed that is customizable by and for each animal care provider and that ultimately enables the animal care provider to benefit from its efforts and be involved in this aspect of the ongoing treatment of the animal.

Such prior art telephone or Internet enabled systems have not been well designed to account for the fact that, in order for a veterinarian to issue a prescription, he or she must first see the animal for which the treatment plan is issued. Therefore, while the telephone or Internet enabled model of distributing veterinary pharmaceuticals has facilitated the distribution of medicines, it still has lacked a viable method for involvement of the veterinary hospital in the offering and selection of products and ultimately the creation of effective animal treatment plans by a veterinarian that is intimately familiar with the animal. Of course, with such prior art systems a veterinarian could call or fax a remote central pharmacy and place a medication order, based on a relatively incomplete system of advance sheets received by the hospital from drug manufacturers, and that order could be shipped to the customer directly by the central pharmacy, but this method has required additional steps for the veterinarian to send the prescription to a remote pharmacy and has lacked a comprehensive system for facilitating customizable product selection by the hospital and individual prescribing veterinarians. Such a system has been needed while managing and facilitating the process and relationship between the hospital and the pharmacy, all while fostering an economic incentive for the veterinarian and hospital to use a particular pharmacy.

In fact, such prior art systems may have introduced a disincentive for better hospital and pharmacy relationships, because once the customer has been introduced to the pharmacy with such prior art, centralized telephone and Internet pharmacy methods, the pharmacy may have developed, and frequently has developed, a direct relationship with the animal owner, selling additional products and services directly to the owner with no supervision and no economic benefit to the veterinarian. Thus, such systems have done little to improve the compliance of administering pharmaceuticals and supplements in accordance with a veterinarian-prescribed treatment plan, since in such case follow through with treatment has still been left almost exclusively to the animal owner.

While the foregoing clearinghouse-type centralized pharmacy solutions have sought to address the inability of veterinarians to effectively and profitably participate in long term treatment plans of animals, as described above, the solutions have entailed other problems, have not provided a comprehensive, yet customizable, means of presenting products for selection by a veterinarian, have not addressed compliance issues as described, and have not adequately involved the veterinarian in the process or transaction, financially or otherwise, sufficient to ensure the high-quality treatment that owners expect for their pets and other animals.

SUMMARY OF THE INVENTION

In accordance with a first aspect of the invention, a computer-enabled method for efficiently displaying a veterinary hospital customizable administrator view of veterinary pharmaceutical and other animal-related product item records is provided. The administrator view is based upon a schema defining a unique product Item_ID field, a plurality of fields corresponding to fields in a centralized pharmacy products database and a plurality of fields corresponding to fields in a hospital managed database. The method comprises the steps of creating an item record in the administrator view from the schema with each of the plurality of fields being undefined, retrieving and storing into the item record in the administrator view at least one item record from the products database, the item record including at least a unique Item_ID field, a Prescription_Required field, a Price field and a Name field, searching the hospital managed database for a corresponding item record for each matching unique Item_ID field to the at least one stored administrator view item record retrieved from the products database, and for each corresponding item record found in the hospital managed database, adding at least one field of the corresponding item record to the administrator view item record.

This aspect of the invention addresses the limitations of the aforementioned prior art manual ordering, prescription writing and fulfilling, as well as telephone or Internet-based centralized animal pharmacies. Of course, since a centralized pharmacy is able to be effectively employed with the invention, the issues of large numbers of products, and specialty products which are not used by a very large number of animals, are greatly minimized. Inventory management is not such a problem with a larger, centralized pharmacy, and the need for constantly updated hard copy advance sheets and drug sales representatives are minimized, since product information is more effectively transmitted to the hospital over the Internet.

Further, since the veterinary hospital is able to participate effectively in the transaction, it is incentivized to build and maintain a good relationship with the centralized pharmacy. This is not only good for business for each party involved, but this also results in more effective service to animal-owner customers, other animal care takers, and their animals.

The steps of the method in accordance with this first aspect of the invention may be applied to create an administrator view for each of a plurality of hospitals, each hospital having a unique Hospital_ID, the unique Hospital_ID being used to filter item record access in the hospital managed database so that the only item records available for use by a particular hospital administrator are those records corresponding to the unique Hospital_ID.

Similarly, the steps of the method may be applied to create an administrator view for a plurality of hospitals in a group, each group having a unique Group_ID, the unique Group_ID being used to filter item record access in the hospital managed database so that the only item records available for use by a particular group administrator are those records corresponding to the unique Group_ID.

Thus, this aspect of the invention allows efficient personalization of per hospital product item preferences without unnecessary duplication of hospital information for a large number of hospitals. Since access to a master product item database is provided by the centralized pharmacy over the Internet to each hospital, the hospital is assisted in staying current product offerings, and with the method of this aspect of the invention, a hospital administrator is able to review the master product item database and select and modify those records desirable to allow either pass through of a particular product to a hospital and/or user view, to prevent a certain product from being presented in such a view, or to allow a product to be presented for hospital or user view but in a modified form. Thus, for example, the hospital administrator could add special veterinary instructions for a product, or a particular product could be offered at a different price than the retail price suggested by the centralized pharmacy. This, in turn, gives the hospital a measure of control over their product offerings and the degree to which the hospital can profit from the sale of the product.

Since each individual hospital's managed database is able to be stored on the central pharmacy's server system, accessible to that hospital via a unique hospital identification code, and since to create the customized product offering to a particular hospital the steps of the method are able to efficiently combine the larger master product item list with the smaller hospital's managed database list to create the hospital's complete view, a large number of hospitals, or groups of hospitals, may be effectively serviced in this way with a minimum of server storage space being required.

The steps of the method may be used to create a list of product item records in the administrator view. Further, the method comprises the steps of rendering editable the Administrator_Detail_View, updating at least one field of the list and saving at least part of a list record to the hospital managed database. These steps of rendering, updating and saving allow the hospital administrator to manage the hospital managed database through list functions, and this further facilitates the ability of the administrator to quickly modify fields of a larger number of products through list processing.

Still further, the steps of the method may be used to create a detailed item record, and the method also comprises the steps of rendering editable the administrator detailed view item record. This allows updating of one or more fields of the detailed item record and saving at least part of the detailed item record to the hospital managed database. These steps of rendering, updating and saving allow the hospital administrator to manage the hospital managed database through detailed item record functions. In this way, the complete information about a product is made available to the administrator so that he or she can make decisions regarding inclusion of the product and related details in the hospital's offering to customers and at what price.

Since the system of the invention allows centralized marketing and hospital customization of product selection by hospital staff and animal owner customers associated with a large number of hospitals, enabling custom product offerings for product sales over the Internet, either with an E-commerce application usable by pet owners at their homes, or at a point-of-sale terminal at the animal hospital, the invention effectively accommodates a large number of smaller, in many cases, and disparate veterinary treatment centers—effectively enabling them to participate in the sale of animal-related pharmaceuticals and products directly to their customers. This, in turn, positively impacts compliance with veterinary treatment programs.

In accordance with another aspect of the invention, a computer-enabled method for efficiently displaying an automatically generated hospital view of veterinary pharmaceutical and other animal related product item records is provided. Each hospital view item record is generated from item records of a products database, each products database item record comprising at least one unique Item_ID field, a Prescription_Required field, a Price field, and a Name field, and selectively modified by item records of a hospital Managed database, each hospital managed database item record having multiple fields comprising at least a unique Item_ID field, an Exclude field, a Price field and a Name field, with at least one hospital managed database item record field optionally containing an overriding value, each hospital view item record having selectively displayed fields. The method of this aspect of the invention comprises the following steps: searching each item record of the products database for a corresponding item record in the hospital managed database and having a matching unique Item_ID field, storing in a hospital view at least part of each item record from the products database not having a corresponding item record in the hospital managed database, not storing in the hospital view any part of each item record from the products database having a corresponding item record in the hospital managed database having the exclude field set to TRUE, and storing in the hospital view an item record having the exclude field set to FALSE and containing at least one field defined by a corresponding field of a corresponding hospital managed database item record and each other field of the hospital view item record defined by a corresponding field of the corresponding products database item record.

In accordance with this aspect of the invention, there is provided an efficient and effective means of creating a view that hospital staff, such as veterinarians, nurses, administrators and other staff members, can use to select pharmaceutical and other animal-related products to easily facilitate the creation of animal treatment plans either before, during or after the prescription writing process. The hospital view provided in accordance with this aspect of the invention draws from a pool of products made available to the hospital staff by the hospital administrator having created the hospital managed product database, the combination of which with the master central pharmacy product database yields the customized hospital view.

In this way the large numbers of products commonly available to treat animals are efficiently managed by a hospital administrator and the products are made readily available to hospital staff. This avoids the need of the hospital to maintain its own pharmacy, thus saving it the cost and effort associated with having to do so, while at the same time giving the hospital access to participate in the product sales chain. This, in turn, yields better care for the animals, since involving a veterinarian in the treatment of the animal is encouraged and further veterinarian treatment plans are more likely to be complied with, because participation of the veterinarian throughout the process is incentivized.

The steps of the method of this aspect of the invention are applicable to create a hospital view for each of a plurality of hospitals, each hospital having a unique Hospital_ID, the unique Hospital_ID being used to filter item record access in the hospital managed database so that the only item records available for use by a particular hospital user are those records corresponding to the unique Hospital_ID.

Further, the steps of the method of this aspect of the invention may be applied to create an hospital view for a plurality of hospitals in a group, each group having a unique Group_ID, the unique Group_ID being used to filter item record access in the hospital managed database so that the only item records available for use by a particular group's users are those records corresponding to the unique Group_ID.

The method of creating a hospital view in accordance with this aspect of the invention may be used to create a list of product item records, and/or a detailed item record, in the hospital view. In this way, the hospital staff can quickly compare one product to another in the list and select the most appropriate product from the list. Or, alternatively, assuming for example that there are multiple products in a list that need authorization by veterinarian, as in a script writing scenario, the multiple products may be efficiently authorized for dispensing, fulfillment and delivery by the veterinarian in a list processing fashion.

The steps of the method of this aspect of the invention may preferably further comprise the step of using the output of the hospital view in a hospital e-commerce website for enabling hospital pet-owner customers to select and purchase only those products previously made available and selectively customized from the products and hospital managed databases. This, in turn, enables users to access the hospital's product offering via the hospital's website. In this way, the value added service provided by the hospital to its customers helps solidify the relationship between the hospital and its customer.

Further still, the steps of the method of this aspect of the invention may preferably further comprise the step of using the output of the hospital view in a hospital client computer system wherein hospital staff may access only those products previously made available and selectively customized from the products and hospital managed databases for product selection in prescription creation and point-of-sale services.

In this way, the customizable product item catalog made available to hospital staff may be used to complete a sale transaction right at the hospital point-of-sale terminal, with product samples being made available to send home with the customer for their animal, and providing for delivery of the rest of the product directly to the customer's doorstep. Again this enables the hospital to effectively make available a very wide range of treatment options and products to customers and to participate in the transaction in a way that better ensures that the veterinarian will be consulted throughout the process and enabled to create and sell an effective treatment regimen to best address the needs of the animal.

The two-tiered construction of a personalized hospital product list aspect of the invention allows simplified global changes to the centralized pharmacy's products database that will automatically update such changes to each hospital view, whether an administrator or a hospital view.

In accordance with another aspect of the invention, a computer-enabled method for efficiently displaying an automatically generated user view of veterinary pharmaceutical and other animal-related product item records is provided. Each view item record is generated from item records of a products database, each products database item record comprising at least one unique Item_ID identifier field, a Prescription_Required field, a Price field, and a Name field. Further, each product item record, and its associated fields, may be selectively modified by item records of a hospital managed database, each hospital managed database item record having multiple fields comprising at least a unique Item_ID field, an Exclude field, a Price field and a Name field. At least one hospital managed database item record field optionally contains an overriding value, and each user view item record has selectively displayed fields. The steps of the method to create the user view comprise the following: searching each item record of the products database having a Prescription_Required field set to FALSE for a corresponding item record in the hospital managed database having a matching unique Item_ID field, storing in a user view at least part of each item record from the products database having the Prescription_Required field set to FALSE and not having a corresponding item record in the hospital managed database, not storing in the user view any part of any item record from the products database having a corresponding item record in the hospital managed database having the exclude field set to TRUE, and storing in the user view at least part of each item record from the products database having the Prescription_Required field set to FALSE, having the Exclude field set to FALSE and containing at least one field defined by a corresponding field of a corresponding hospital managed database item record and each other field of the user view item record defined by a corresponding field of the corresponding products database item record.

The steps of method of creating a user view in accordance with this aspect of the invention preferably further comprise the step of using the output of the user view in a hospital e-commerce website for enabling hospital pet-owner customers to select and purchase only those products previously made available and selectively customized from the products and hospital managed databases.

Also, the steps of the method in accordance with this aspect of the invention may be used to create a list of product item records, and/or a detailed item record, in the user view.

Since the system of the invention allows practice of marketing, product selection and product sales over the Internet, either with an E-commerce application usable by the pet owner at his or her home, or at a point-of-sale terminal at the animal hospital, with convenient delivery of the ordered product to the customer's doorstep, the invention effectively accommodates a large number of smaller, in some cases, and disparate veterinary treatment centers—effectively enabling them to participate in the sale of animal-related products directly to their customers—thus positively impacting compliance with veterinary treatment programs.

This aspect of the invention is primarily intended for products not requiring a prescription authorization from the veterinarian hospital, such as supplements, feeds, over-the-counter treatment regimens and the like. However, this aspect of the invention may enable a user to purchase re-fills of already authorized pharmaceuticals as well. For example, a veterinarian may authorize a heartworm medication for an animal that may be renewable for six months. If the customer didn't want to purchase all six months in advance, he or she could access the hospital's website through a secure account to purchase pre-authorized refill medications for which the animal has already been seen by the veterinarian.

Since in accordance with the present invention the veterinarian is conveniently placed at the center of the supply of pharmaceuticals and other products in the processes of the invention, the veterinarian is supported in providing better care to the animal and in enabling better compliance by the animal owner with treatment plans. This coherent, comprehensive, veterinarian-centric method and system of supplying animal-related products to animal owners for administering treatments to their animals fosters appropriate and best practices for practicing veterinarian medicine. From generation of customizable and customized catalog views for hospital administrators, hospital staff and customer users, the catalog generating system dovetails with prescription drafting systems and the auto-generation of shipment records and the automated delivery of products to the animal owner, the veterinarian, the animal hospital, the animal owner and the animal are all supported in a more efficient and seamless strategy for treatment.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

BRIEF DESCRIPTION OF THE DRAWINGS

FIG. 7a is a schematic representation of a partial record layout for application of the processes of FIGS. 6a and 6b, and the routine of 6e, to create a pass through record for presentation in a view;

FIG. 7b is a schematic representation of a partial record layout for application of the processes of FIGS. 6a and 6b, and the routine of 6d, to exclude a product database record for presentation in a view;

DETAILED DESCRIPTION

System Overview

Figure 1:
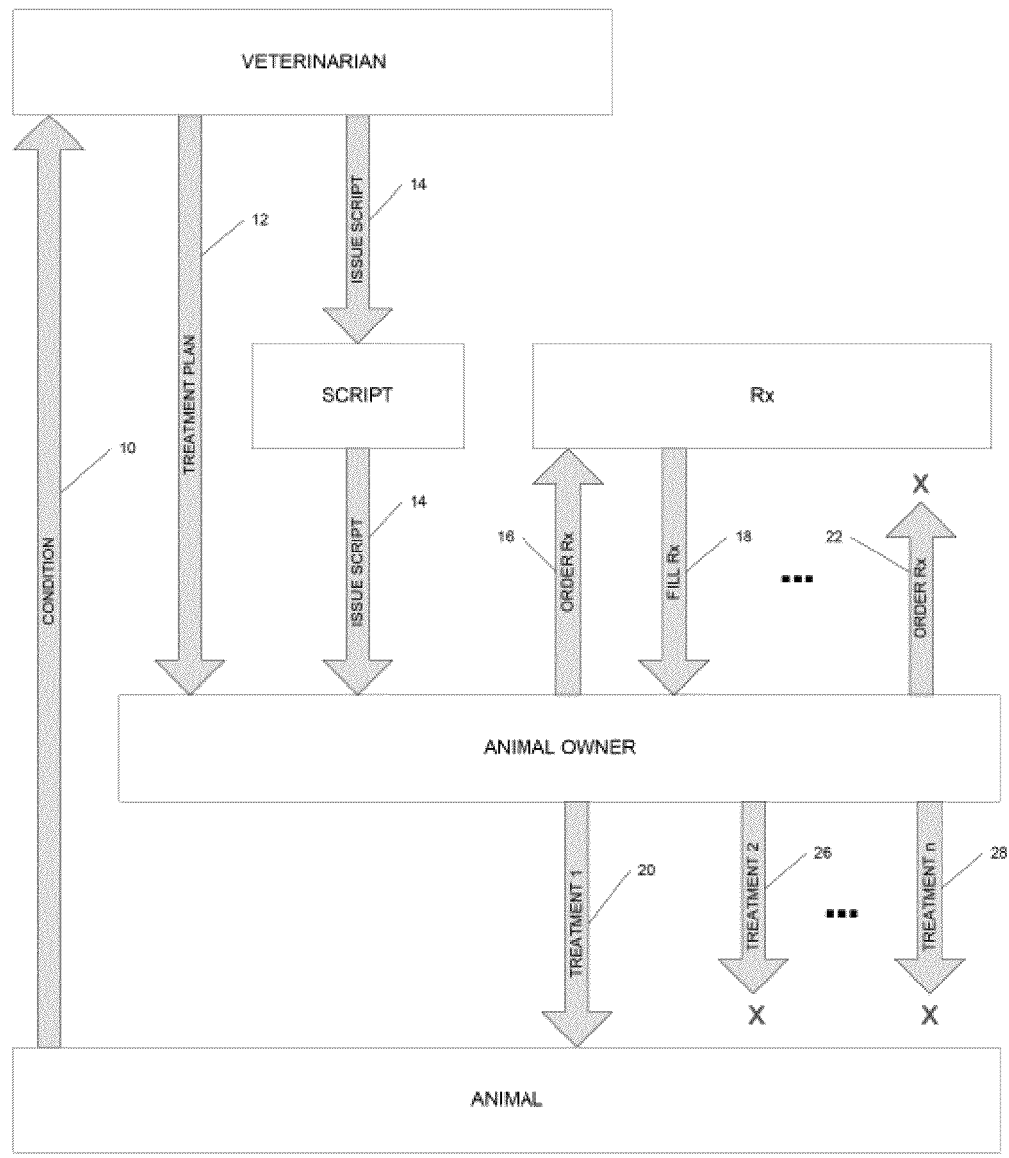
FIG. 1 is a schematic representation demonstrating compliance and noncompliance with a veterinarian's treatment plan in connection with a prior art method and system for treatment of animals.
Figure 2:
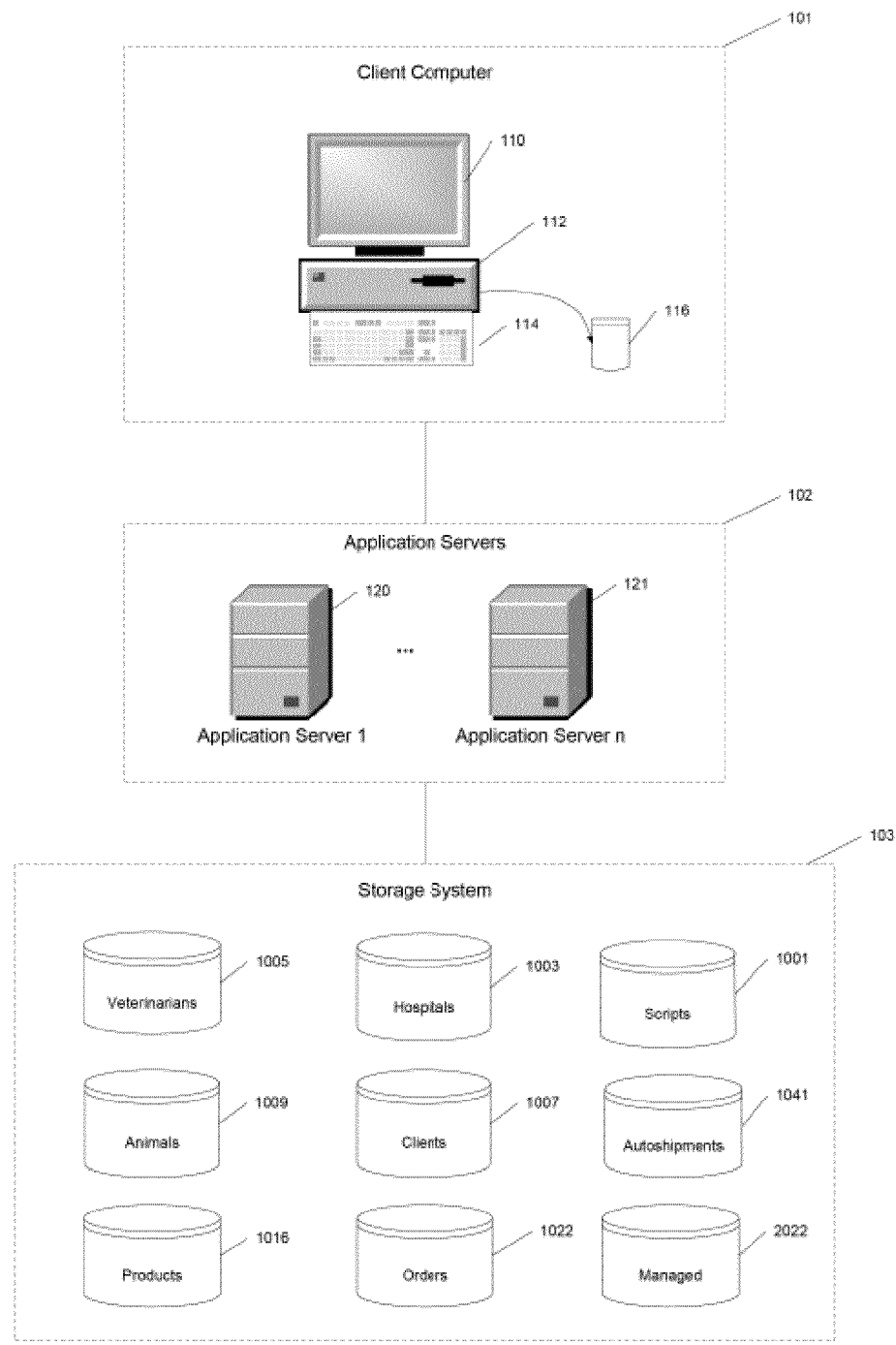
FIG. 2 is a schematic representation of a client server system with a supporting data storage system in accordance with which a preferred embodiment of the invention is practiced.

Referring to FIG. 2, client computer system 101 is one of a plurality of such client computer systems being located at a veterinarian hospital, or plurality of hospitals, including any animal treatment facility or location where a licensed veterinarian is authorized to do business, and the server system 102 with supporting data storage system 103 may support many such hospitals having such plurality of client computer systems 101.

While each client computer system 101 preferably comprises a traditional monitor 110, processing hardware 112, keyboard 114, mouse 116, application software, Internet software and hardware components (not shown), it will be appreciated by those of ordinary skill in the art that any computer system, such as a smart phone, hand-held device, laptop, or other equivalent computing device with adequate memory and processing capability will satisfy the client computer system for purposes of the present invention. Further, multiple client computer systems 101 may be networked, for example on an Ethernet-type network within a hospital complex, the networked systems being represented in whole by client computer system 101 as is well understood by those of ordinary skill in the art. Further, it will be appreciated by those of ordinary skill in the art that, since many veterinarians work independently, the invention may be used by individual veterinarians by considering the veterinarian and the hospital to be one and the same in the database.

Client computer systems 101 may run any type of client computing operating system and software, such as Windows®, that enables access by the user of the client computer system to the Internet and the ability to process application data within the client portion of the application software of the invention on the client computer system.

One or more application servers 102, comprising parallel processing, mirrored, or RAID configured servers 120, 121, etc., run the server side portion of the application software of the invention and provide secure access to data in the storage system 103. Servers 102 may comprise a plurality of servers that are housed in a single location where the size of the system permits and there exists sufficient power and security to meet reliability and availability needs. The servers 102 are preferably interconnected to each other and to data storage system 103 by a high-speed local networking system. Servers 102 are also connected to the plurality of client computers 101 via the Internet.

Storage system 103 preferably comprises a redundant array of magnetic storage media disk drives, optical storage system, or the like, capable of the fast access and retrieval times necessary to accommodate many requests in rapid succession from the multiple client computer systems 101 and application servers 102.

Storage system 103 houses a plurality of databases corresponding with key elements of data preferable for veterinarians at their respective hospitals to generate animal treatment plans, including creation of any prescriptions necessary, from hospital managed and customizable product item record views generated in accordance with the present invention, for fulfillment and autoshipment to the customer by the central pharmacy.

In accordance with the present invention, the central pharmacy provides a master product database 1016 for each hospital administrator to access via an administrator view. The hospital administrator accesses database 1016 via an administrator workstation or login at a staff workstation to create records as desired within a hospital managed customization database 2022. Thus, after a particular hospital administrator creates records within his or her hospital managed customization database 2022, this customization database 2022 is used in conjunction with the central pharmacy provided master product database 1016 to generate a hospital customized view. The hospital customized view is the way in which veterinarians and staff gain access to and select products in generating animal treatment plans and prescriptions.

These prescriptions and animal treatment plans are then used to generate autoshipment records for automated delivery of animal-related products and pharmaceuticals directly to customers. Thus, the key elements of data preferable for the operation of the overall system comprise scripts database 1001, hospitals database 1003, veterinarians database 1005, clients database 1007, animals database 1009, products database 1016, autoshipments database 1031, orders database 1022 and hospital Managed database 2022.

Data Structures

Figure 3A:
FIG. 3a is an entity relationship diagram illustrating the databases of an overall system for creating and fulfilling veterinary prescription and other animal-related product orders and in which the hospitals, hospital managed and products databases of the present invention interact.

Referring to FIG. 3a, which comprises a more detailed view of the databases of the overall storage system shown in FIG. 2, and which is illustrated in entity relationship diagram (ERD) notation. In particular, FIG. 3a shows how the hospitals database 1003, the products database 1016 and the hospital Managed database 2022 of the invention relate to the other databases of the system, including generally clients database 1007, veterinarians database 1005, scripts database 1001, animals database 1009 and orders database 1022. While the hospital Managed database 2022 and the hospitals database 1003 of the invention specifically relate with other databases of the overall system per standard ERD notation, as shown by arrows drawn between them and the foreign keys designated "FK1", "FK2", etc., the products database 1016 has no arrows between it and the other databases of the system because per standard ERD notation there are no foreign key references in the products database from any other database in the system, and it relates to the other databases of the system only through specific processes described further herein to create views in accordance with the present invention. These databases comprise an overall data structure residing in a self-synchronizing relational database, such as in a Structured Query Language database server.

Thus, as shown in FIG. 3a, each record in the products database 1016 comprises a unique, computer-generated primary key, Product_ID, that is associated with the following fields: Item_ID, Name, Image, Description, Price, and Prescription_Required, as shown. While the Product_ID field is a unique, computer-generated primary key, one Product_ID for each product item record in the products database 1016, the Item_ID field is a skew number that uniquely identifies a product as it would be inventoried, including brand, quantity, size, potency, etc. The values held in the other fields of the products database are as their field names suggest.

Each record in the hospitals database 1003 comprises a unique, computer-generated primary key, Hospital_ID, that is associated with the following fields: Name, Address, Billing_Info and Email, as shown. The values held in the fields of the hospitals database are as their field names indicate.

Each record in the hospital Managed database 2022 comprises a unique, computer-generated primary key, Managed_ID, which primary key uniquely describes that hospital managed database item record and is associated with the following other fields: Hospital_ID, Product_ID, Exclude, Name, Price, Image and Description, as shown.

Accordingly, it will be appreciated from looking at FIG. 3a that, for example in hospital Managed database 2022, each record has a Hospital_ID that includes a foreign key (FK1) that references a particular record for that hospital in the hospitals database 1003 as shown by the arrow pointing from the hospital Managed database to the hospitals database.

As will be apparent to those of ordinary skill in the art, only the key elements or fields of the hospital managed, products and hospitals databases, as well as the other databases of the overall system, have been shown and described, and it will be apparent to such persons that these records may be expanded to include additional pertinent information about the unique items each database describes. Further, it will be appreciated that the names of each field in each database is not limited to the names shown in a preferred embodiment, but that any database field functioning in the same way would fall within the scope of the claims appended hereto.

Figure 3B:
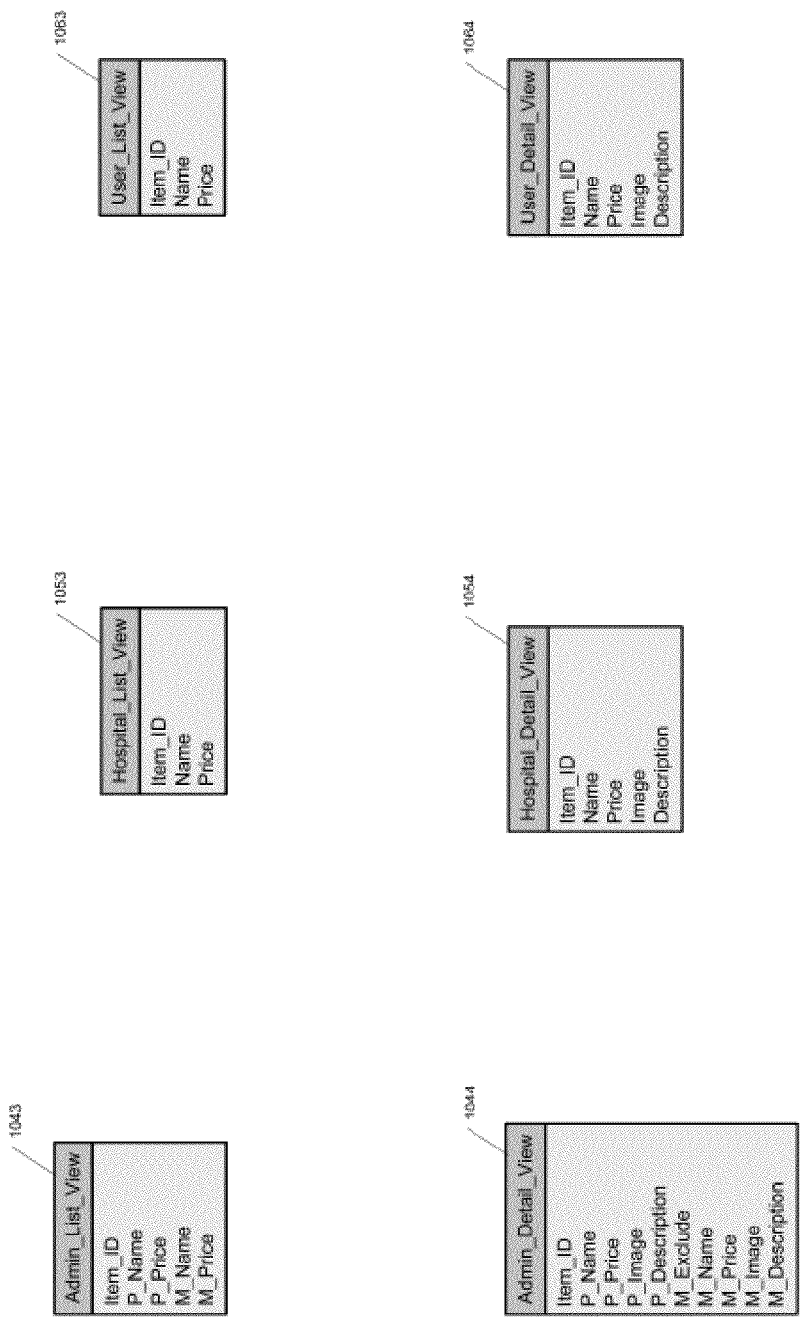
FIG. 3b is an entity relationship diagram illustrating the schema for dynamically generated views in accordance with the present invention.

FIG. 3b illustrates in detail a plurality of schema for dynamically generated views, including Admin_List_View 1043, Admin_Detail_View 1044, Hospital_List_View 1053, Hospital_Detail_View 1054, User_List_View 1063 and User_Detail_View 1064.

Admin_List_View 1043 preferably comprises schema for the following field names: Item_ID, P_Name, P_Price, M_Name, and M_Price, where the prefix P_ designates a field name for a value retrieved from the products database 1016, the prefix M_ designates a field name for a value retrieved from the hospital Managed database 2022 and Item_ID designates a field name referring to corresponding data in the field Item_ID for the products database 1016 and the field Item_ID in the hospital Managed database 2022 in FIG. 3a.

Admin_Detail_View 1044 preferably comprises schema for the following field names: Item_ID, P_Name, P_Price, P_Image, P_Description, M_Exclude, M_Name, M_Price, M_Image and M_Description. As stated above in connection with view schema 1043, the prefix P_ designates a field name for a value retrieved from the products database 1016, the prefix M_ designates a field name for a value retrieved from the hospital Managed database 2022. Further, Item_ID in schema view 1044 refers to the same type of identification as described above.

Hospital_List_View 1053 preferably comprises schema for the following field names: Item_ID, Name and Price.

Hospital_Detail_View 1054 preferably comprises schema for the following field names: Item_ID, Name, Price, Image and Description.

User_List_View 1063 preferably comprises schema for the following field names: Item_ID, Name and Price.

User_Detail_View 1064 preferably comprises schema for the following field names: Item_ID, Name, Price, Image and Description.

Administrator Operations

Figure 4:
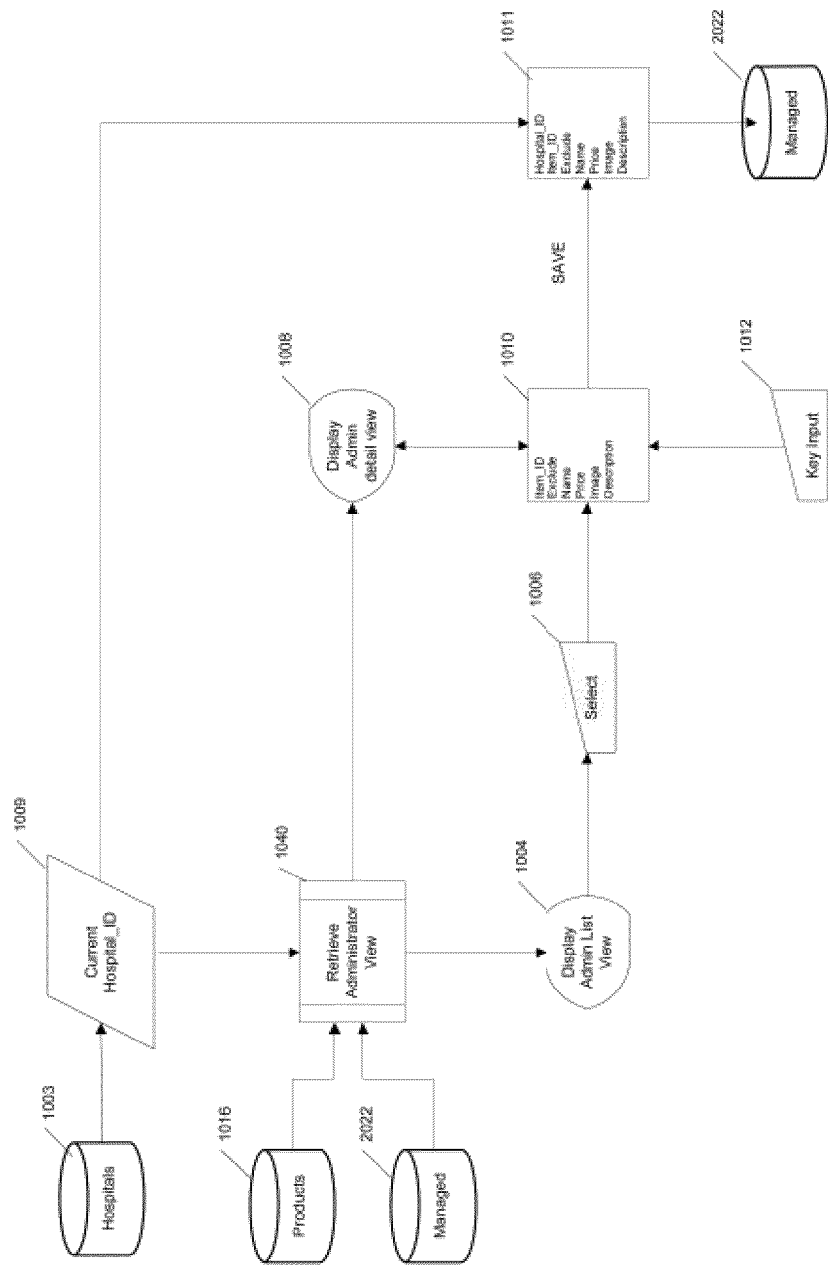
FIG. 4 is a schematic diagram illustrating a process for a hospital administrator to manage and maintain a hospital managed catalog in a hospital Managed database in accordance with the present invention.

Referring now to FIG. 4 there is shown the process a hospital administrator follows for retrieving product records into an Administrator_List_View 1004 or Administrator_Detail_View 1008 in order to create and/or modify corresponding product records, if any and to the degree desirable, in the hospital managed database 2022.

As shown, the current Hospital_ID 1009 is retrieved at login and maintained in memory while the login is active. The current Hospital_ID 1009 corresponds to a unique hospital identifier in the Hospitals database 1003, it is stored for later use in computer readable memory at 1009 at the time of login, and it is used later in the process of saving a modified record 1011 as further described below. Once an Administrator_List_View 1004 has been retrieved, edits may be made to values in the list view itself. A particular item record as detailed in FIG. 9, may be selected at 1006 for retrieval and display in a new Administrator Detailed View as shown at 1008. At the same time, the corresponding item record 1010 is opened for edit as shown at 1012. For example, the administrator is enabled to change the exclude status of the record, or he or she can change the name, description or price of the item that is displayed in subsequent user views. The administrator is then enabled to save the newly modified record 1011, together with the Hospital_ID, in the hospital managed database 2022. Any previously saved record having a matching Item_ID and Hospital_ID in the hospital managed database is overwritten by the aforementioned process. Since the process that saves and retrieves item records in the hospital managed database uses both an Item_ID and a Hospital_ID associated with the record, the system thus guarantees that the there is only one such record for the current hospital that matches the criteria for saving and retrieval of the record. In this way, the integrity of the database is assured.

Generate Administrator Views

Figure 5A:
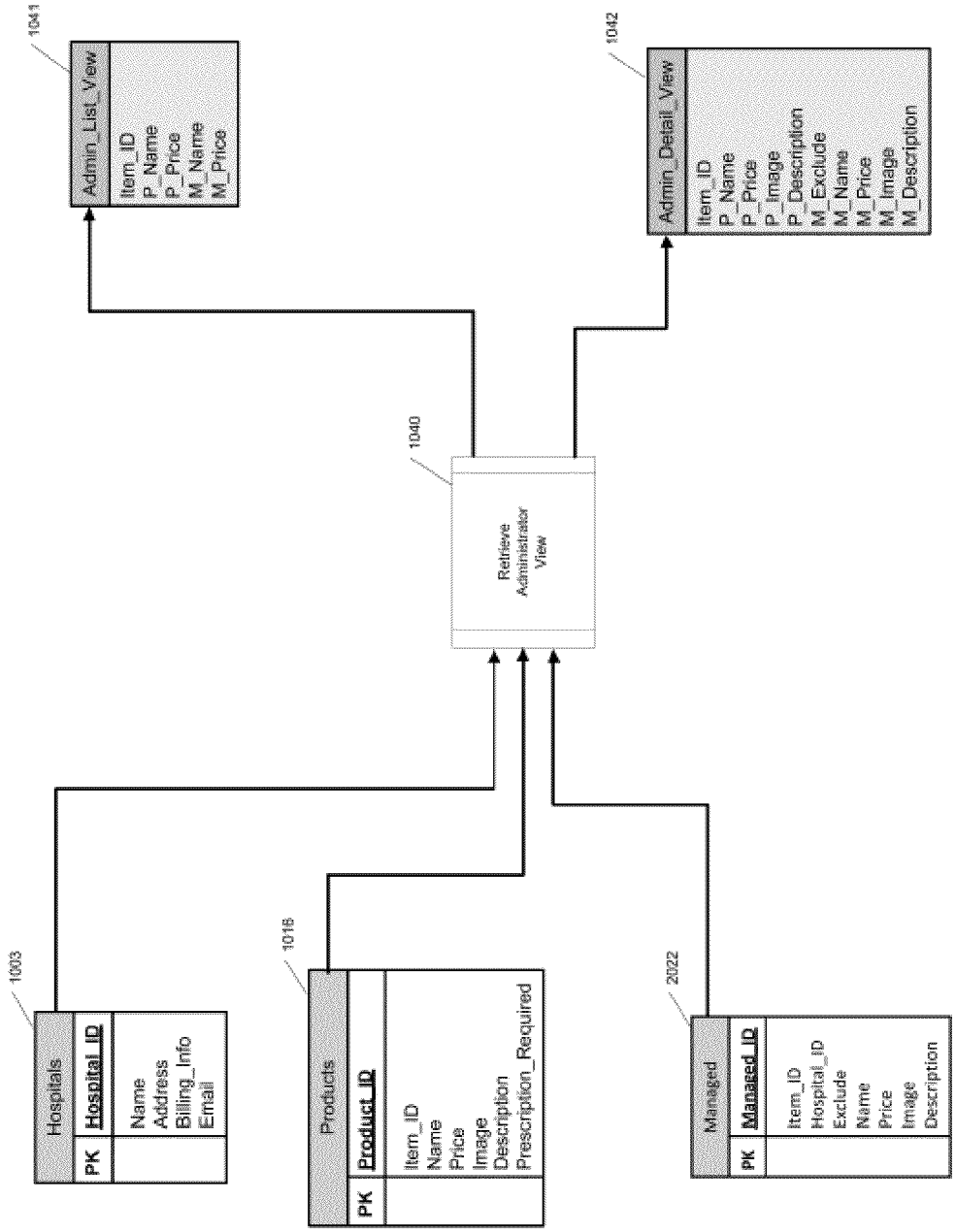
FIG. 5a is a high-level process diagram illustrating the relationship between databases and an internal computer process in accordance with an aspect of the invention for creating an administrator view.

The display of an administrator view, or in other words the retrieval of an administrator view as shown at 1040, whether it be an Admin_List_View 1004 or an Admin_Detail_View 1008, is described in further detail in FIG. 5a.

Figure 8:
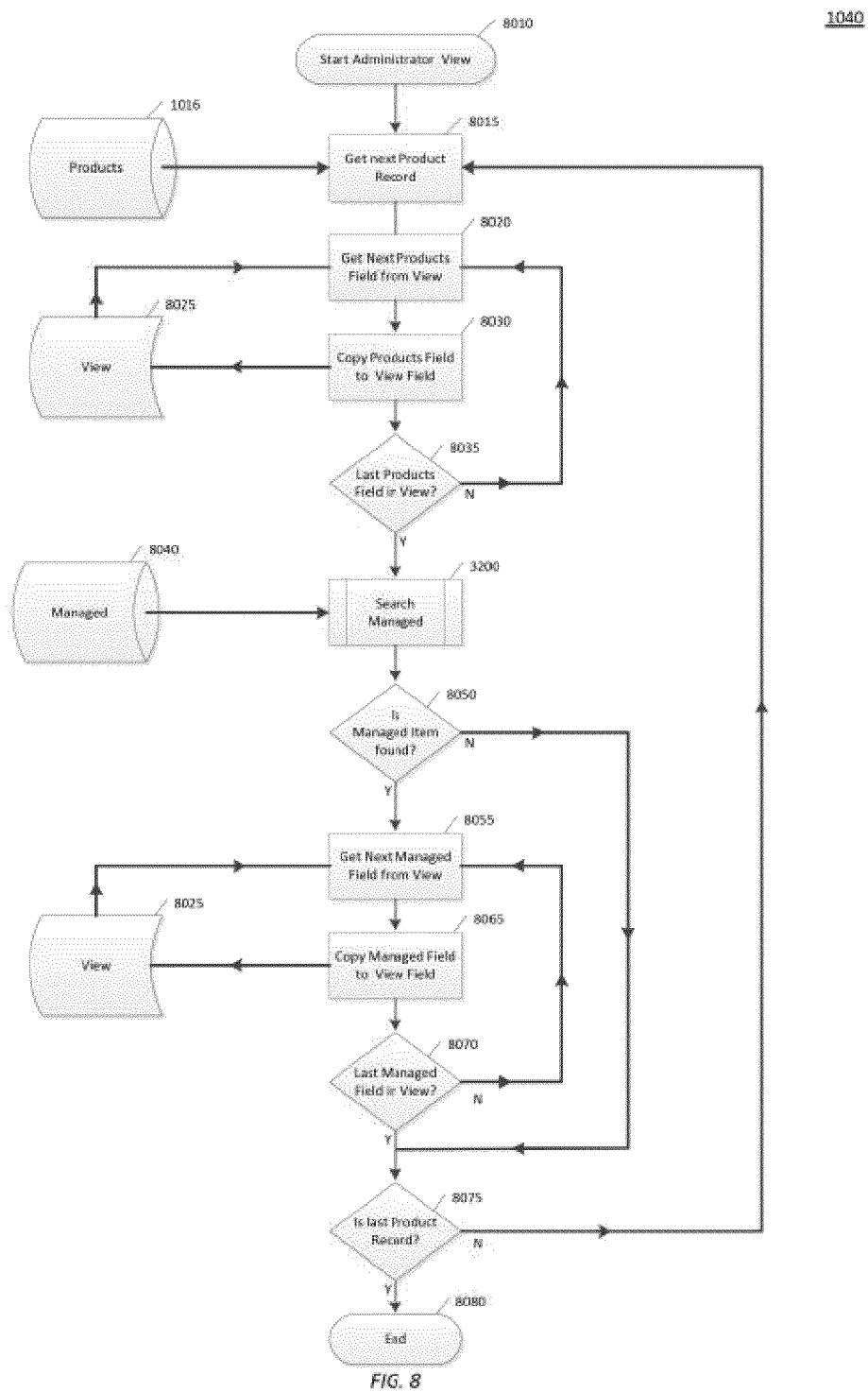
FIG. 8 is a flowchart diagram detailing the internal computer process for creating an administrator view in accordance with the present invention.

Referring to FIG. 5a, the administrator views Admin_List_View 1041 and Admin_Detail_View 1042 are view records generated from their respective schema 1043 and 1044 and populated by a combination of fields from the Hospitals database 1003, the Products database 1016 and, optionally, the hospital Managed database 2022 through a process as defined at 1040 that is further described in FIG. 8.

Referring to FIG. 8, there is shown a flowchart outlining the process of populating administrator views 1041 and 1042. At 8015 the next (or first) product record is retrieved from the Products database 1016. Boxes 8020, 8030 and 8035 form a loop in which the fields of an administrator view 8025, which have a corresponding field in the product record retrieved at 8015, are populated with the values of the corresponding fields. This loop is repeated until the last products field specified by the view is populated as shown at 8035.

Administrator views for the purpose of FIG. 8 may either be an Administrator List view 1041 or an Administrator_Detail_View 1042 as seen on FIG. 5a. Since the two types of administrator views 1041, 1042 have differing numbers of fields, the loop comprised of boxes 8020, 8030, 8035 will execute the proper number of times to populate whatever number of fields are available according to the schema for the view. This mechanism allows the user of the system to change the view to suit his or her needs without re-coding the system processes.

Figure 6A:
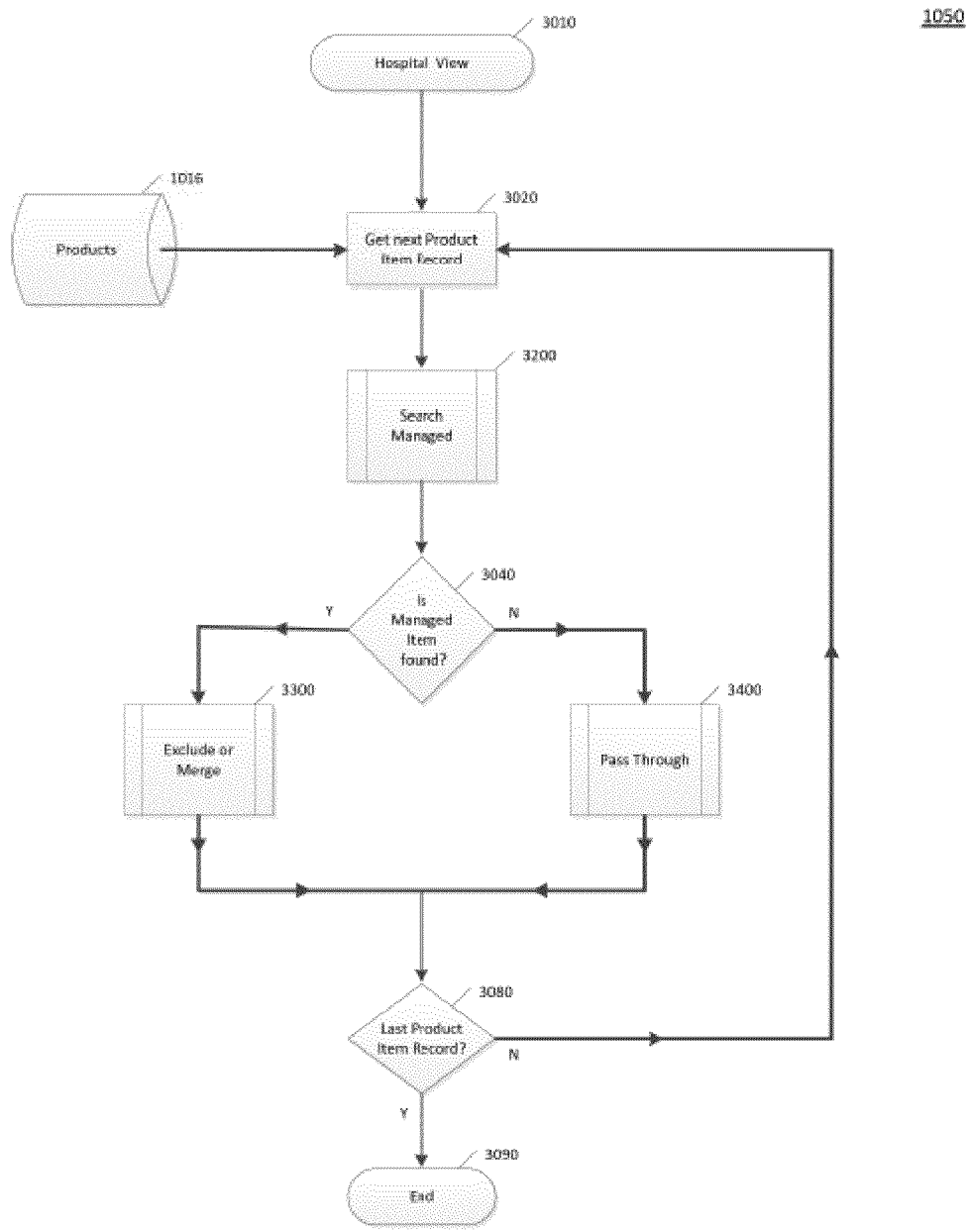
FIG. 6a is a flowchart diagram detailing the internal computer process of FIG. 5b for creating a hospital view in accordance with the present invention.
Figure 6B:
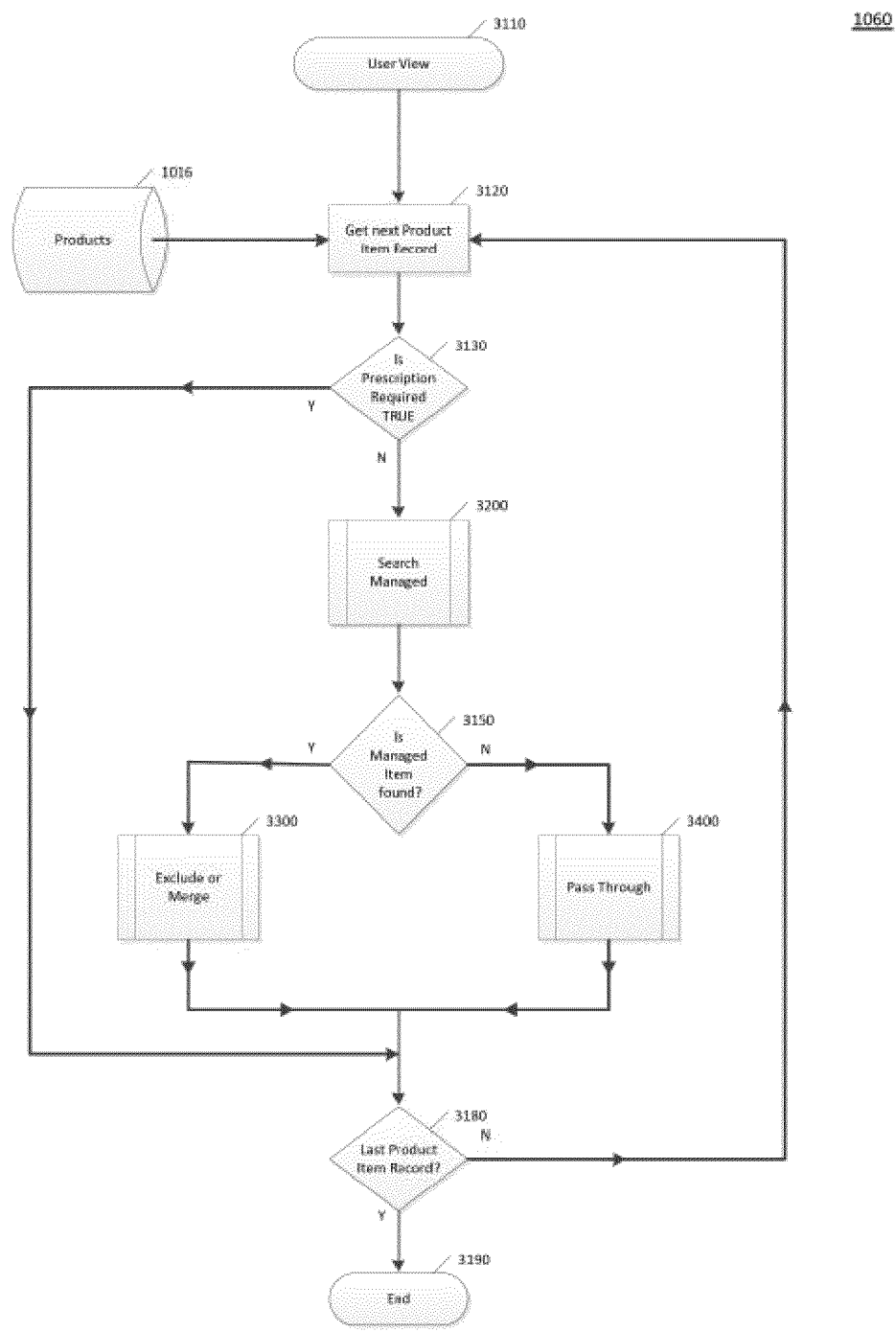
FIG. 6b is a flowchart diagram detailing the internal computer process of FIG. 5c for creating a user view in accordance with the present invention.
Figure 6C:
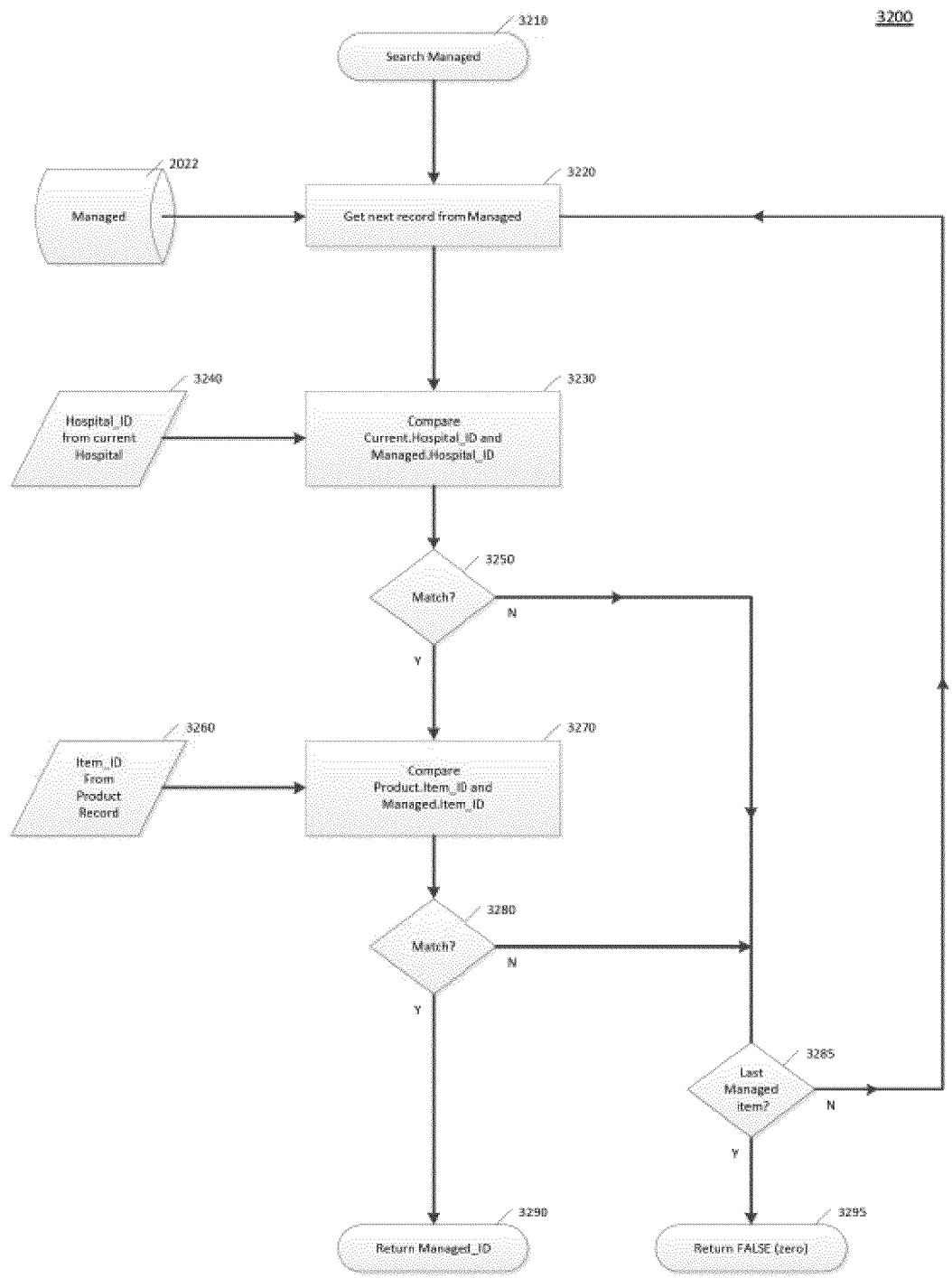
FIG. 6c is a flowchart diagram of a search hospital Managed database routine used by the process of FIG. 6a in accordance with the present invention.

At subprocess box 3200 a search managed subprocess shown and described hereafter in connection with FIG. 6c is called for the purpose of determining if any hospital managed records exist for the current hospital that have a matching product Item_ID to the currently retrieved product record Item_ID.

If a record is found in the subprocess 3200 described in connection with FIG. 6c, a loop comprised of boxes 8055, 8065 and 8070 of FIG. 8 is processed in which the schema generated fields 1041, 1042 of the administrator view 8025, which have a corresponding field in the hospital managed record retrieved at 8050, are populated with the values of the corresponding fields. This loop is repeated until the last hospital managed field specified by the view is populated as shown at 8035.

Finally, at 8075, the Administrator View process determines if there are any more records to process in the Products database. If so, control is returned back to the beginning of the process at 8015 to repeat for the next Product item record. If not, the Administrator View process is complete as shown at 8080 and an administrator view, whether it be a list view or a detailed view, has been completed.

Figure 9:
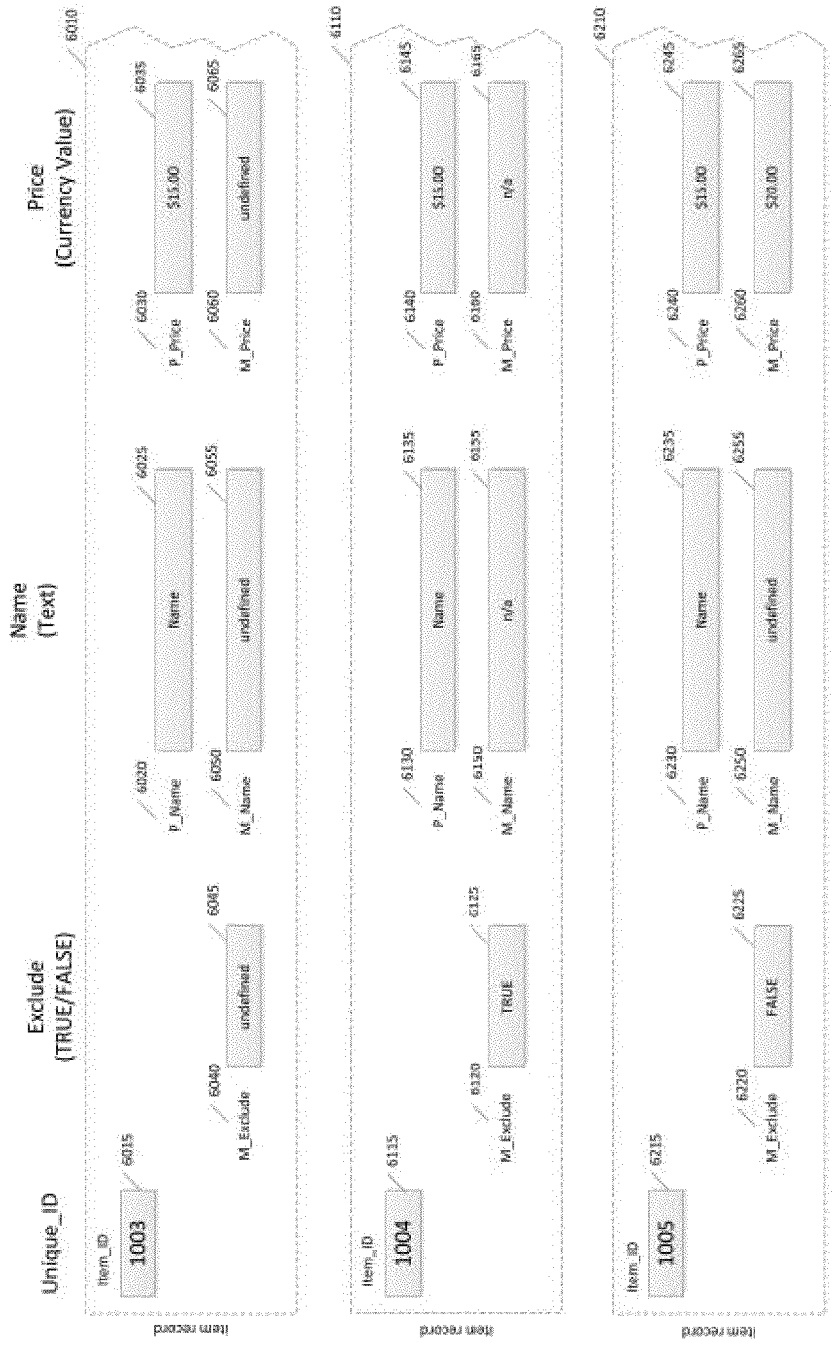
FIG. 9 is a schematic representation of a partial record layout of administrator view item records as displayed for the purpose of administrator management and editing of a partial pass through item record, a partial exclude item record and a partial modified item record.

Referring to FIG. 9, an administrator view of three item records is shown to illustrate how records from the Products database 1016 and the Managed database 2022 are presented in the administrator view. Referring to item record 6010 having the Item_ID 1003, which incidentally is a pass through type record as further described herein, the product record on the upper line, designated with fields preceded with P_, such as P_Name 6020 and P_Price 6030, is displayed for administrator review. Further, in the same item record 6010, there is displayed for administrator view and edit a corresponding item record from the hospital Managed database 2022, designated with fields preceded with M_, such as M_Exclude, M_Name and M_Price.

As an administrator views a particular Item record 6010, 6110, 6210, he or she is enabled to edit the hospital managed portion of the record, such as that shown at Item_ID 1004 where the administrator has set the M_Exclude field to TRUE to indicate the administrator's preference that that particular record not be presented to either a hospital view or a user view later on.

Similarly, if the administrator wishes to override the price of a particular item, he or she may do so as shown at Item_ID 1005, as shown where M_Price of that record has been edited by the Administrator to increase the price of the item from $15.00 to $20.00 to indicate the administrator's preference that that particular item be merged with the product database item record, but at a higher retail sales price by the hospital.

Thus, an administrator may easily, with a minimum of edits and additions to the hospital managed database, make available a customized version of the master Product database catalog from the centralized pharmacy that will be viewed by staff and customers of the hospital.

Generate Hospital Views

Figure 5B:
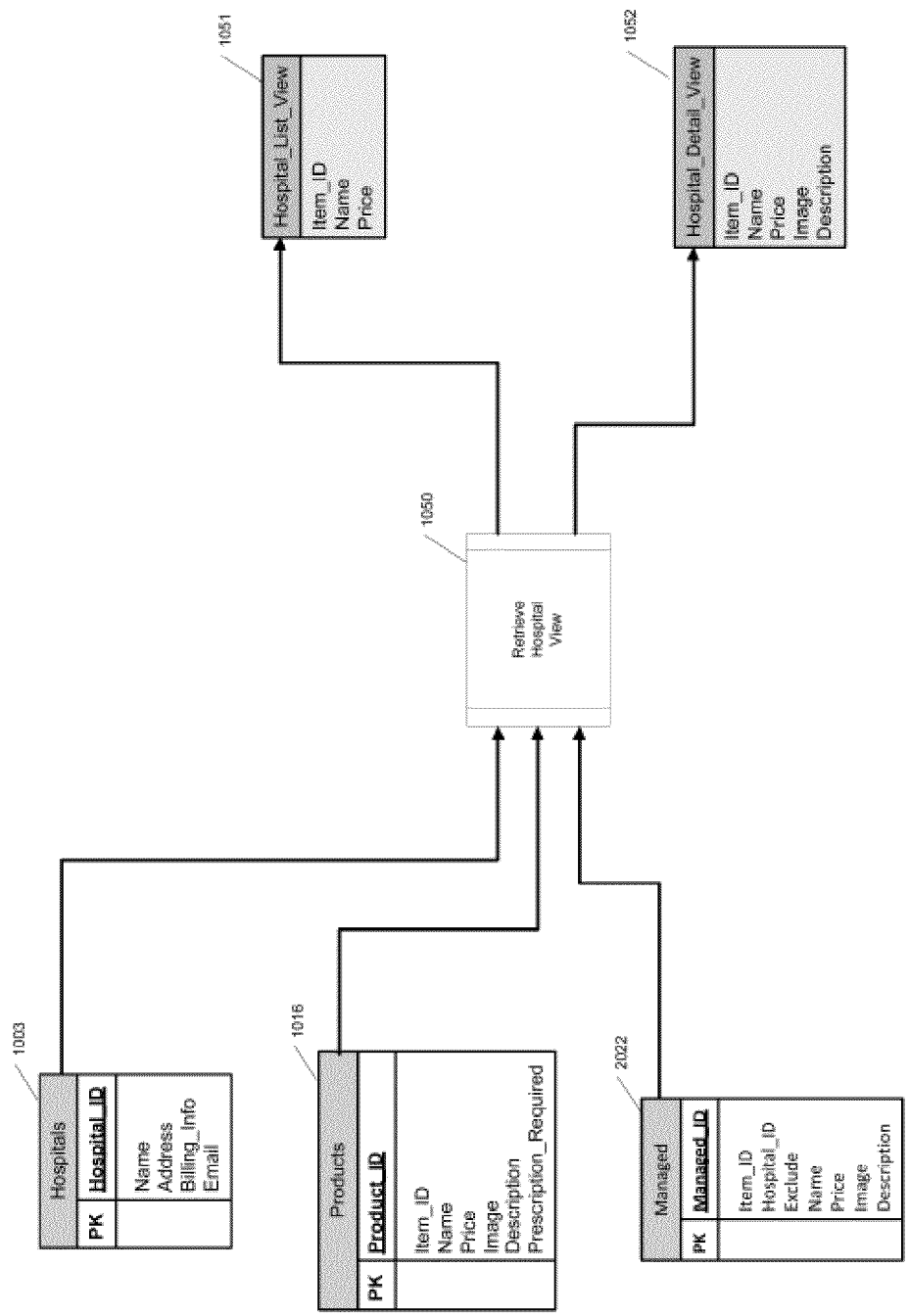
FIG. 5b is a high-level process diagram illustrating the relationship between databases and an internal computer process in accordance with another aspect of the invention for creating a hospital view.

Referring to FIG. 5b, the display of a hospital view, or in other words the retrieval of a hospital view as shown at 1050, whether it be a Hospital_List_View 1051 or a Hospital_Detail_View 1052 is shown. The hospital views Hospital_List_View 1051 and Hospital_Detail_View 1052 are view records generated from their respective schema 1053 and 1054 and populated by a combination of fields from the hospitals database 1003, the Products database 1016 and, optionally, the hospital Managed database 2022 through a process as defined at 1050 that is further described in connection with FIG. 6a.

Figure 6D:
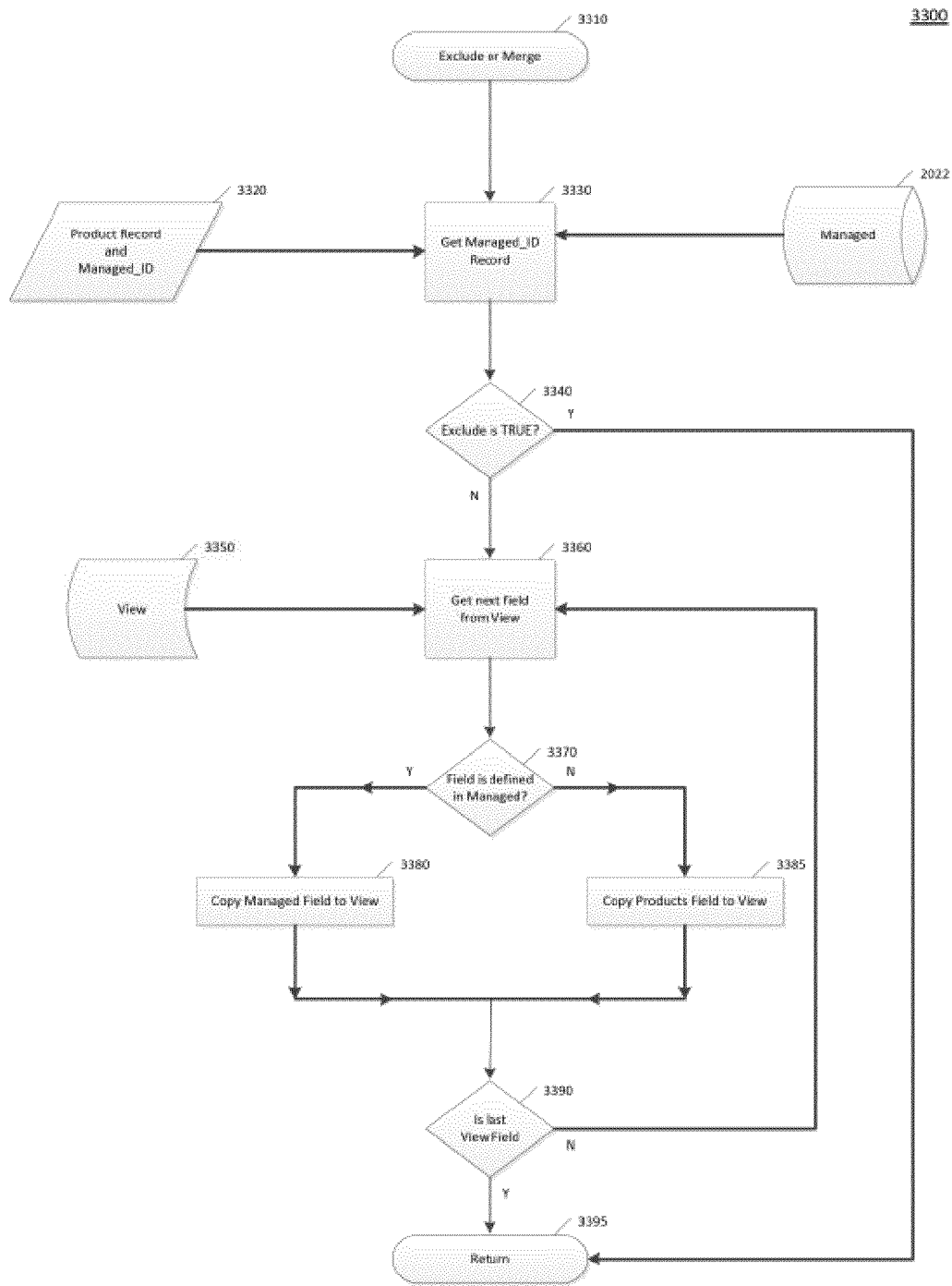
FIG. 6d is a flowchart diagram of an exclude/merge routine used by the processes of FIGS. 6a and 6b in accordance with the present invention.
Figure 6E:
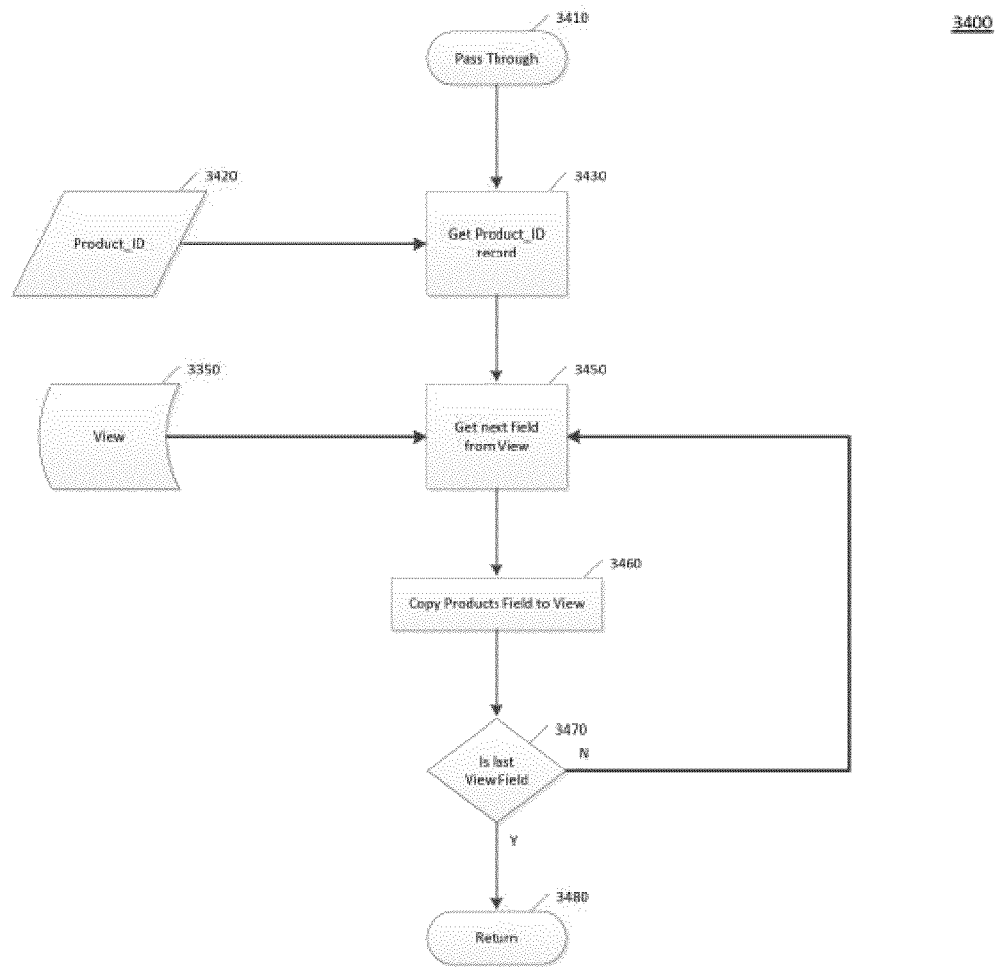
FIG. 6e is a flowchart diagram of a pass through routine used by the processes of FIGS. 6a and 6b in accordance with the present invention.

Referring to FIG. 6a, there is shown a flowchart outlining the populate hospital view process 1050 for populating hospital view 3350 through subprocesses exclude/merge 3300 or pass through 3400 (see FIGS. 6d and 6e). Boxes 3020 and 3080 form a loop which cycles through the Products database 1016 and looks for matching managed records by calling a search managed subprocess 3200 which either returns the Managed_ID of an item record found in the hospital Managed database 2022 or returns a zero, null or equivalent value indicating that no record was found. Based upon the return value in process 3200, the populate hospital view process 1050 then branches at 3040 to the exclude/merge subprocess 3300 if a Managed_ID record number is returned. If a zero or null value was returned, indicating no managed record was found, then 3040 passes control to the pass through subprocess 3400. Whether subprocess process 3300 or 3400 was called, when the subprocess is completed, it returns control to process 1050 at decision block 3080. At block 3080, process 1050 checks to see if the current item record is the last item record to be processed. If not, process 1050 is repeated to get the next item record for processing. If so, the process 1050 terminates at 3090 and the hospital view 3350 is complete.

Generate User Views

Figure 5C:
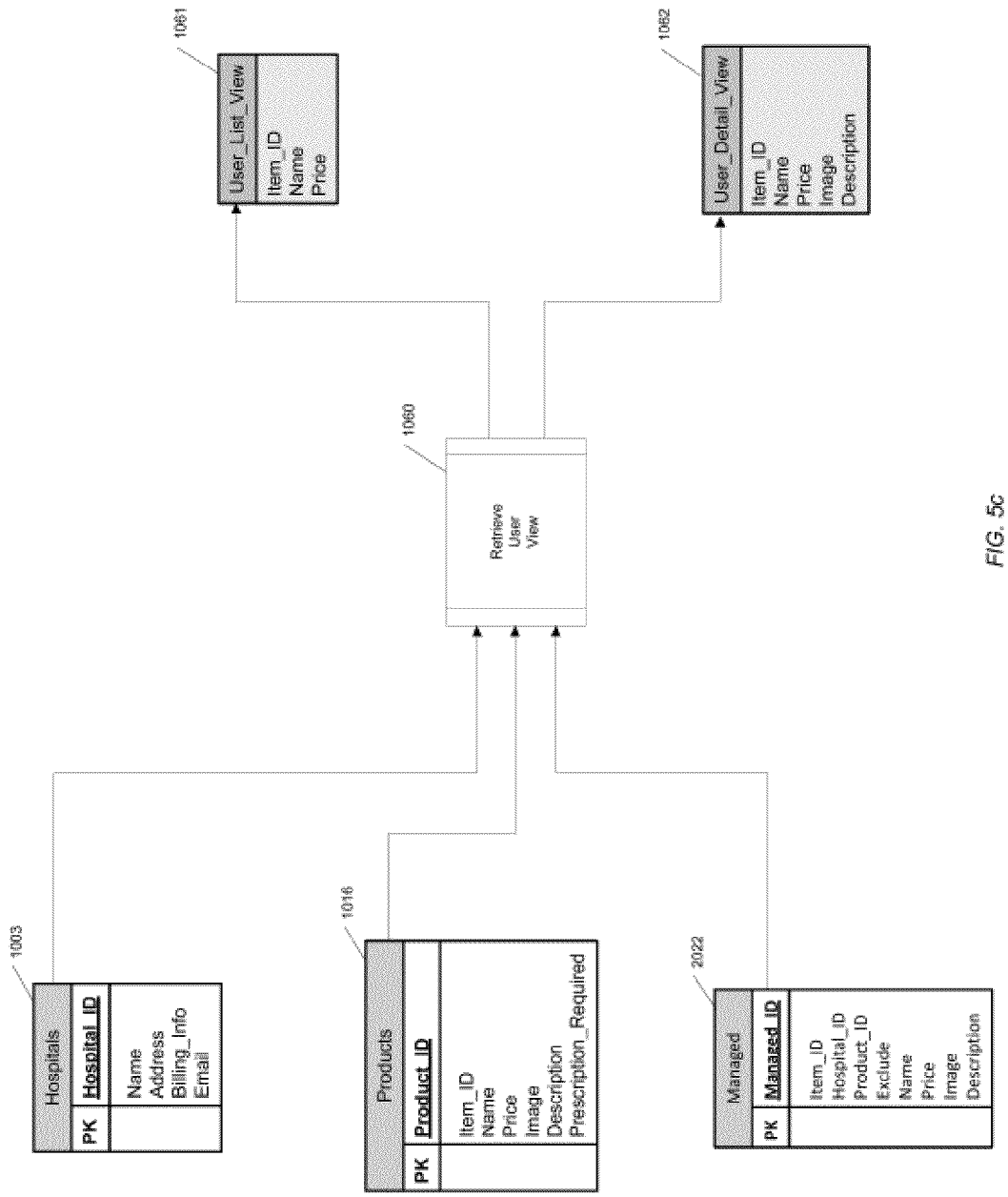
FIG. 5c is a high-level process diagram illustrating the relationship between databases and an internal computer process in accordance with another aspect of the invention for creating a user view.

Referring to FIG. 5c, the display of a user view, or in other words the retrieval of a user view as shown at 1060, whether it be a User_List_View 1061 or a User_Detail_View 1062 is shown. The user views User_List_View 1061 and User_Detail_View 1062 are view records generated from their respective schema 1063 and 1064 and populated by a combination of fields from the Hospitals database 1003, the Products database 1016 and, optionally, the hospital Managed database 2022 through a process as defined at 1060 that is further described in FIG. 6b.

Referring to FIG. 6b, there is shown a flowchart outlining the populate user view process 1060 for populating user view 3350 through subprocesses exclude/merge 3300 or pass through 3400 (see FIGS. 6d and 6e). Boxes 3120 and 3180 form a loop which cycles through the Products database 1016 to retrieve the first (or next) record of the database 1016. As a preliminary step, at 3130, the populate user view process 1060 checks to see if a Prescription_Required field of the retrieved record is set to TRUE. If so, then this record is for a pharmaceutical that requires a prescription and it therefore would not be appropriate to include in the user view that is primarily intended for retail sales. Therefore, process 1060 passes control to decision diamond 3180 to determine whether the last item record of the Products database has been considered. If another record is to be considered, the process 1060 returns control to process box 3120 to get the next record and the process 1060 continues with the rest of the steps of the process. If the Prescription_Required field is FALSE process 1060 continues and looks for a matching managed record by calling a search managed subprocess 3200, which either returns the Managed_ID of an item record found in the hospital Managed database 2022 or returns a zero, null or equivalent value indicating that no record was found. Based upon the return value in process 3200, the populate user view process 1060 then branches at 3150 to the exclude/merge subprocess 3300 if a Managed_ID record number is returned. If a zero or null value was returned, indicating no managed record was found, then 3150 passes control to the pass through subprocess 3400. Both subprocesses 3300, 3400, when completed, return control to process 1060 at decision block 3180. At block 3180 process 1060 checks to see if the current item record is the last item record to be processed. If not, process 1060 is repeated to get the next item record for processing. If so, process 1060 terminates at 3190 and the user view 3350 is complete.

Subprocesses

Search-Managed Subprocess

Referring to FIG. 6c, the Search Managed subprocess 3200 comprises a loop that scans through the hospital Managed database 2022 to find a matching record that has a Hospital_ID that matches the current hospital and a Managed Item_ID that matches the Product Item_ID in question. The subprocess can terminate in two different ways as shown at 3290 and 3295: 1) if it finds a matching record, it will return to the calling process the Managed_ID value corresponding to the record found as shown at 3290, or 2) if no record is found, the subprocess will return a zero, null, FALSE or other equivalent value to indicate there is no matching record in the hospital Managed database 2022 as shown at 3295.

More specifically, referring to FIG. 6c, the Search Managed subprocess 3200 comprises the following steps: At 3220, the first (or next) record is retrieved from the hospital Managed database 2022. The current Hospital_ID found in memory 3240 based upon the current login session is then compared to the Hospital_ID in the currently retrieved hospital managed database record to see if there is a match. Comparing the Hospital_ID from memory 3240 to the Hospital_ID in the currently retrieved hospital managed database item record, ensures that the subprocess is only considering data from the correct, current, hospital and not other hospitals that may be concurrently using the system. At 3250, the match is checked, and if there is no match the system determines at 3285 if the currently considered record of the hospital Managed database 2022 is the last record. If it is the last record, then the subprocess exits and returns a FALSE as shown at 3295 to the calling process. This occurs when the entire hospital Managed database 2022 has been searched for a matching record, and none is found. If it is not the last record, then control is passed to the Search Managed subprocess 3200 at 3220 to repeat the process on the next hospital managed record. If, on the other hand, a match is found at 3250, control is passed to the compare block 3270 where the Product Item_ID of the current product record received from the calling process as shown at 3260 is compared with the Item_ID of the current record retrieved from the hospital Managed database 2022. If the Product Item_ID and the Hospital Item_ID match, then the subprocess 3200 terminates at 3290 by returning the found record's Managed_ID from the Hospital Managed database to the calling process. Thus, it will be appreciated that as soon as a match is found, the process 3200 terminates as described because, per the design of the system, there is one, and only one, record in the Hospital Managed database having a matching value for the data in the Hospital_ID field and the Item_ID field.

Exclude or Merge Subprocess

Figure 7C:
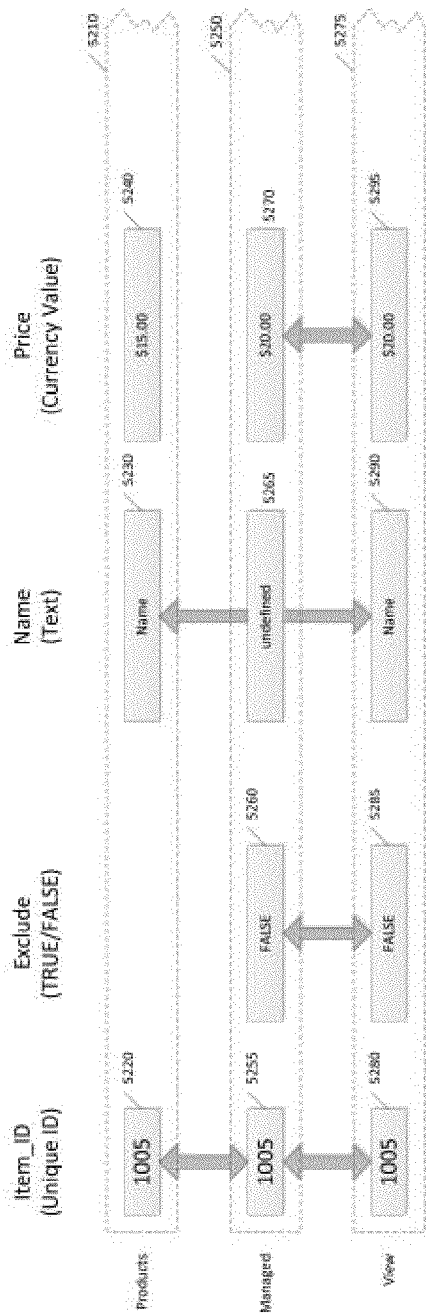
FIG. 7c is a schematic representation of a partial record layout for application of the processes of FIGS. 6a and 6b, and the routine of 6d, to create a view record having a modified price field.

Referring to FIGS. 6d, 7b and 7c, the Exclude or Merge subprocess 3300 is called by either the Hospital View process 1050 or the User View process 1060 such that a found Managed_ID in either of those processes is passed to the Exclude or Merge subprocess and the current product record is stored in computer readable memory as shown at 3320. At 3330 the aforementioned Managed_ID is used to retrieve the entire record from the Managed database 2022 for use in the subprocess 3300. At 3340, the subprocess 3300 determines whether the exclude field of the retrieved record is set to TRUE. If the exclude field of the retrieved record is set to TRUE, then neither this record, nor the corresponding record from the Products database 1016, will be included in the view to effectuate a hospital administrator's decision to remove the corresponding product from the hospital's catalog. Accordingly, control is transferred to 3395, and this subprocess 3300 returns control to the calling process with no further action being taken by the subprocess. If in 3340, the exclude field is determined to be FALSE, at least one field from the retrieved record, in combination with fields from the Products database record will be copied to the view 3350 until each field in the view has been populated. Process boxes 3360 through 3390 comprise a loop in which each schema generated field in the view 3350 is checked to determine if a corresponding Managed database field value is defined or undefined as shown at 3370. If defined, as shown at 3380, the corresponding Managed database field value is copied to the view field. If undefined, as shown at 3385, the corresponding Product database field value is copied to the view field. In either case, control is returned to decision process 3390 to check whether the previously populated field was the last field in the view. If not, control is returned to process 3360 to get the next field in the view 3350. If the previously populated field was the last field in the view, the loop is terminated and control is returned to the calling process as shown at 3395.

In the context of the Exclude or Merge subprocess 3300, views 3350 may comprise either a Hospital_List_View 1051, a Hospital_Detail_View 1052 (FIG. 5b), a User_List_View 1061 or a User_Detail_View 1062 (FIG. 5c) generated from their respective schema 1053, 1054, 1063, 1064 as shown on FIG. 3b. It should be obvious to those of ordinary skill in the art that these schema may be modified to include fewer or more fields without requiring any change to the subprocess 3300.

Referring to FIG. 7b the Exclude portion 3340 (FIG. 6d) of the Exclude or Merge subprocess 3300 is further illustrated with an example products record 5110 and its corresponding managed record 5150, wherein the value in the Item_ID 5120 for the Products record 5110 is the same as the Item_ID 5155 for the Managed record 5150, and the exclude field 5160 is set to TRUE. Thus, as described above in connection with the Exclude or Merge subprocess 3300, the Product record 5110 is not included in the view 5190 as indicated by the X's shown in the view. In FIG. 7b view 5190 is a specific instance of a view, such as view 3350 shown in FIG. 6d. As shown at the right hand side of the view, those of ordinary skill in the art will appreciate that there may be other fields in each of the aforementioned records.

Referring to FIG. 7c, the Merge portion starting at 3360 (FIG. 6d) of the Exclude or Merge subprocess 3300 is further illustrated with an example Products record 5210 and its corresponding Managed record 5250, each record having the same unique Item_ID, and in which Managed record's exclude field is set to FALSE. As illustrated, where field, such as the Name field 5265 is undefined in the Managed record, the value from the Name field 5230 of the Product record 5210 passes through to the view field 5290 of the view record 5275 during the Merge portion of the Exclude or Merge subprocess 3300. As further illustrated with the Price fields 5240, 5270, where the Managed record 5250 contains a value in the Price field 5270, the value in the Managed record is passed to the Price field 5295 of the view 5275. Thus, the resulting view record 5275 is "merged" as it comprises one or more fields from each the Product record 5210 and the Managed record 5250. As shown at the right hand side of the view, those of ordinary skill in the art will appreciate that there may be other fields in each of the aforementioned records that may or may not be expressed in a given view.

Pass Through Subprocess

Referring to FIG. 6e, the Pass Through subprocess 3400 is called by either the Hospital View process 1050 or the User View process 1060 because a matching Managed record was not found in either process 1050, 1060. When the subprocess 3400 is called it is passed a Product_ID 3420 indicating the entire product record which is retrieved at 3430 from the Products database 1016 and which is used to populate the view 3350. At 3450, 3460, 3470, a loop is formed in which each successive field of the view 3350 is populated from the corresponding field in the retrieved Product record. This loop is repeated until the last field specified by the view is populated as determined at 3470. Once the view is populated the subprocess 3400 is terminated as shown at 3480 and control is returned to the calling process.

Referring to FIG. 7a, the Pass Through subprocess 3400 is further illustrated by example with a Products record 5010 existing in the Products database 1016, but a corresponding Managed record (shown by dotted lines and reference number 5050) does not exist as there is no record with a corresponding Item_ID for the current hospital found in the Managed database 2022. Accordingly, as illustrated, the Item_ID field 5020, the Name field 5030 and the Price field 5040 of the Products record 5010 are passed through to the view 5060. As shown at the right hand side of the view, those of ordinary skill in the art will appreciate that there may be other fields in each of the aforementioned records that may or may not be expressed in a given view.

In the context of the Pass Through subprocess 3400, views 3350 may comprise either a Hospital List view 1051, a Hospital Detailed view 1052 (FIG. 5b), a User List view 1061 or a User Detailed view 1062 (FIG. 5c) generated from their respective schema 1053, 1054, 1063, 1064 as shown on FIG. 3b. It should be obvious to those of ordinary skill in the art that these schema may be modified to include fewer or more fields without requiring any change to the subprocess 3400.

Scaling Considerations and Advantages

Figure 10A:
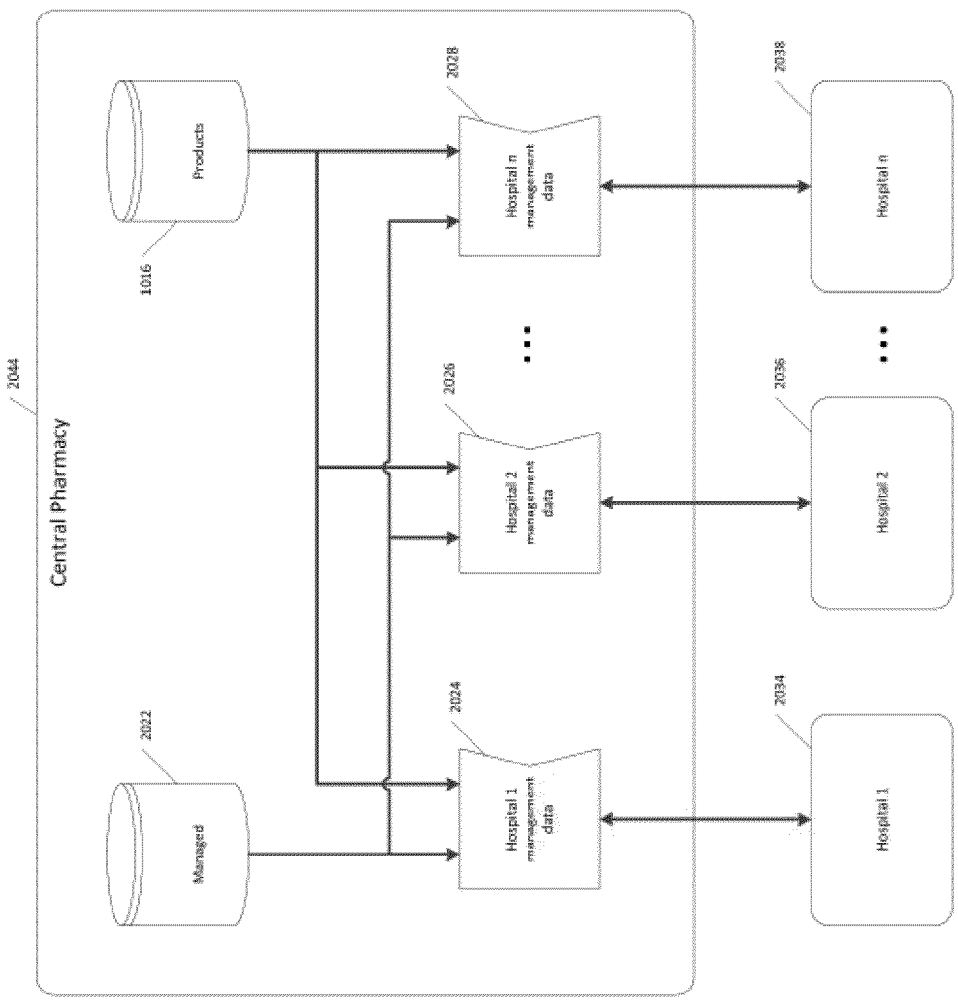
FIG. 10a is a schematic representation of a preferred embodiment of the system of the invention as used by a centralized pharmacy to service multiple hospitals.

Referring to FIG. 10*a*, a preferred embodiment of the invention is shown wherein the system of the invention is implemented with a centralized pharmacy 2044 to service multiple hospitals 2034, 2036, 2038. Accordingly, there is a single hospital managed database that contains the management records for each hospital serviced by the pharmacy. For example, as shown, hospital Managed data 2024 belongs to Hospital 1 2034, Hospital 2 Managed data 2026 belongs to Hospital 2 2036, and Hospital n (where n represents the number of the hospital data of the total number of hospital's data contained in the database) Managed data 2028 belongs to Hospital n 2038.

This aspect of the invention addresses the fact that a busy central pharmacy not only services a potentially large number of hospitals, but the pharmacy also contains data for a very large number of products. Where a single product item record in a database of product items may contain several hundred fields, it will be readily appreciated that the size of such a central pharmacy database would be very large. Accordingly, because the system of the present invention provides for a single, and relatively large, master Products database from the central pharmacy, with only exception-type customization databases associated with each hospital, database server storage space is minimized and processing speed is enhanced. In other words, each hospital simply provides its relatively small hospital managed database to the centralized pharmacy and the system is designed to create customized catalogs for each hospital based upon a minimum of data from the hospital. This not only saves server space and processing efficiency, but also is easier for each hospital administrator to manage, as only a relatively few records are needed to indicate exclusion of unwanted or modified items.

Figure 10B:
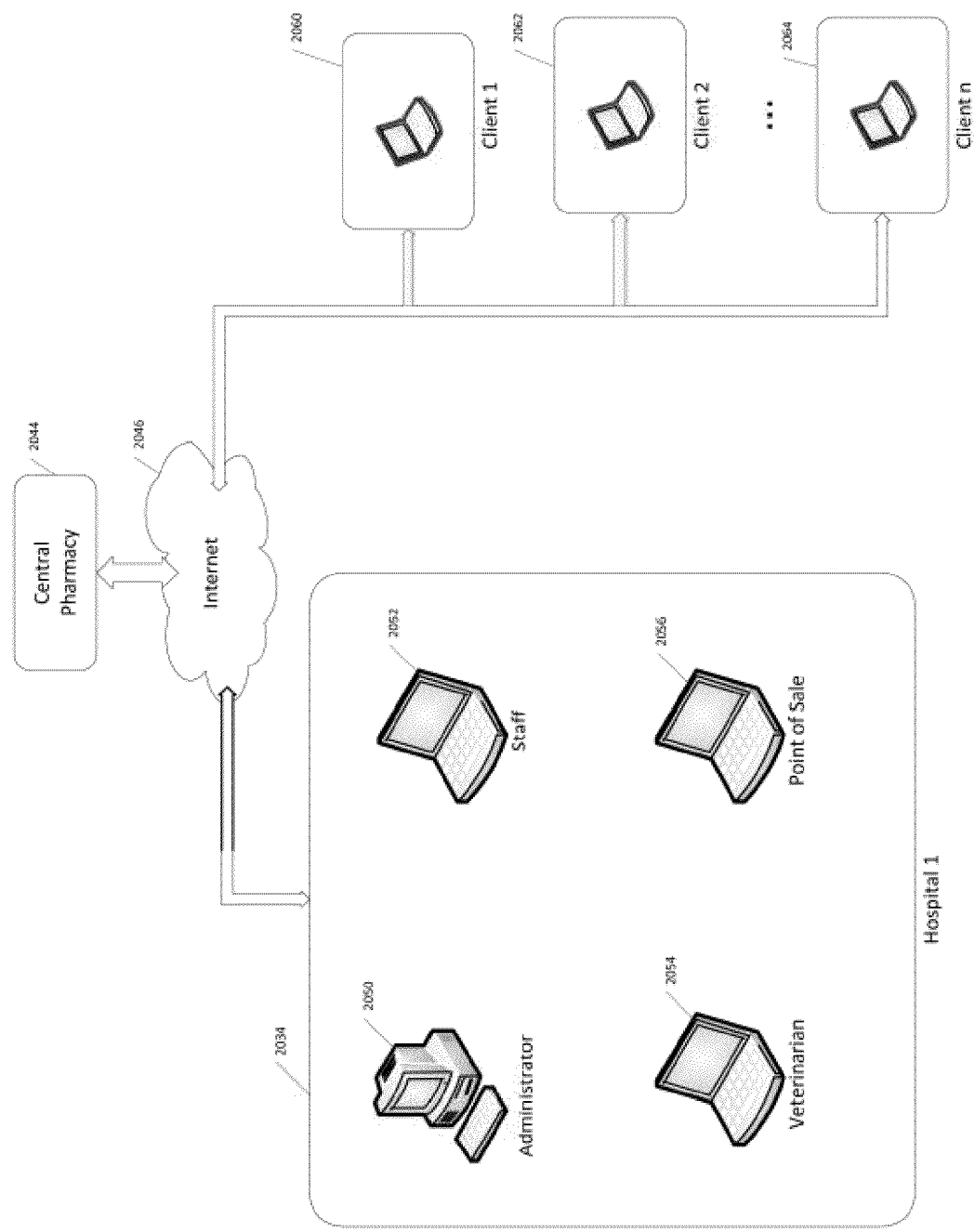
FIG. 10b is a schematic representation of a veterinary hospital, together over the Internet with a central pharmacy, to display to internal users and online customers a hospital managed, customizable, e-commerce catalog.

Referring to FIG. 10*b*, once a particular hospital 2034 creates a hospital Managed database (2022—not shown), another aspect of the invention comprises the ability of the hospital to provide multiple terminals at the hospital, including an administrator terminal 2050, staff terminals 2052, veterinarian terminals 2054 and even point-of-sale terminals 2056 to allow for sale of products and pharmaceuticals to customers, and each such terminal access point to the database views only the data intended for that hospital in accordance with the customized hospital managed database created by a hospital administrator.

Since access to the central pharmacy 2044 is provided via the Internet 2046 with the present invention, customers or clients 2060, 2062, 2064 of each hospital, for example hospital 2034, are enabled to access a website for the hospital to purchase products over the Internet via an e-commerce system. Indeed, this aspect of the invention allows a hospital to relatively easily have and maintain an e-commerce website that may preferably, or optionally, be provided by the centralized pharmacy as a service to the hospital for display and purchase of such products by the customer. As described above, in connection with the point-of-sale 2056 and staff terminals 2052, the e-commerce website and associated remote customer access terminals would see only those products in the hospitals catalog as customized by a hospital administrator.

Figure 10C:
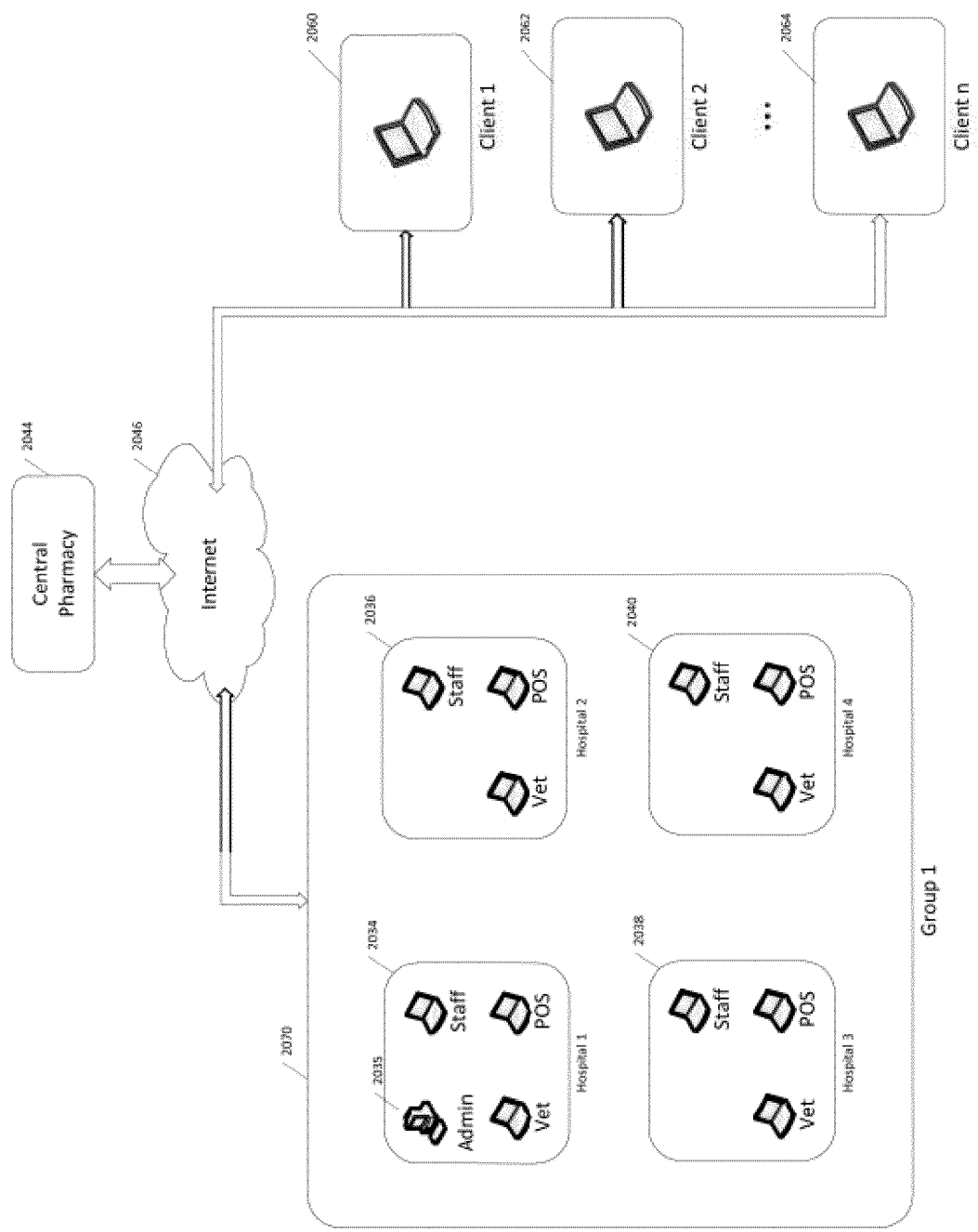
FIG. 10c is a schematic representation of a group of veterinary hospitals, together over the Internet with a central pharmacy, to display to internal users and online customers a centrally-managed, customizable, e-commerce catalog.

Referring to FIG. 10*c*, a group 2070 of hospitals 2034, 2036, 2038, 2040 is shown that is serviced by a single administrator 2035, and accordingly, each hospital in the group accesses the same customized catalog as would a single hospital as shown and described in connection with FIGS. 10*a* and 10*b*. Similarly, client 1 2060, client 2 2062, and client n 2064 (where n represents a particular client of the total number of a hospital group's clients), are enabled to access a website for the group of hospitals to purchase products over the Internet via an e-commerce system provided, preferably by the pharmacy, for the group. This aspect of the invention allows a group of hospitals to relatively easily have and maintain an e-commerce website as a service to customers of the group of hospitals for display and purchase of products by the customer. The e-commerce website and associated remote customer access terminals would see only those products in the group's catalog as customized by the commonly shared group administrator.

Those of ordinary skill in the art will appreciate that presentation of an Internet-based, e-commerce website will involve an HTML server with HTML web pages, etc. Further, it will be appreciated that the present invention may be used in networked environments other than the Internet, such as electronic mail messaged systems, local area networks, wide area networks, and point-to-point dialup networks. Further, it will be appreciated that any combination of hardware and software provided by an animal products provider or pharmacy that is capable of allowing customized generation of catalogs as described is intended to fall within the claims of the present invention.

Further, it will be appreciated by those of ordinary skill in the art that, depending upon implementation, different database servers will have varying methods for generating data structures, such as views. In the case of the present invention, the most generic sense of the term view is intended. In other words, the terms "views" and "view maintenance" refer more generically to data structures in computer readable memory and the programs that initialize and maintain them, respectively, as well as direct calls for a view from the database operating system.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

What is claimed is:

1. A computer-enabled method for efficiently displaying a veterinary hospital customizable administrator view of veterinary pharmaceutical and other animal related product item records, the administrator view comprising a schema defining a unique item identifier field, a plurality of fields corresponding to fields in a centralized pharmacy managed products database and a plurality of fields corresponding to fields in a hospital managed database, comprising the steps of:

creating an item record in the administrator view from the schema with each of the plurality of fields being undefined;

retrieving and storing into the item record in the administrator view at least one item record from the products database, the item record including at least a unique item identifier field, a prescription required field, a price field and a name field;

searching the hospital managed database for a corresponding item record for each matching unique item identifier field to the at least one stored administrator view item record retrieved from the products database; and for each corresponding item record found in the hospital managed database, adding at least one field of the corresponding item record to the administrator view item record.

2. The method of claim 1, wherein the steps of the method are applied to create an administrator view for each of a plurality of hospitals, each hospital having a unique hospital identifier, the unique hospital identifier being used to filter item record access in the hospital managed database so that the only item records available for use by a particular hospital administrator are those records corresponding to the unique hospital identifier.

3. The method of claim 1, wherein the steps of the method are applied to create an administrator view for a plurality of hospitals in a group, each group having a unique group identifier, the unique group identifier being used to filter item record access in the hospital managed database so that the only item records available for use by a particular group administrator are those records corresponding to the unique group identifier.

4. The method of claim 1, wherein the steps of the method are used to create a list of product item records in the administrator view.

5. The method of claim 4, further comprising the steps of:
rendering editable the administrator view item record list;
updating at least one field of the administrator view detailed item record list; and
saving at least part of the administrator view detailed item record list to the hospital managed database; wherein said steps of rendering, updating and saving allow the hospital administrator to manage the hospital managed database.

6. The method of claim 1, wherein the steps of the method are used to create a detailed item record in the administrator's view.

7. The method of claim 6, further comprising the steps of:
rendering editable the administrator view detailed item record;
updating at least one field of the administrator view detailed item record; and
saving at least part of the administrator view detailed item record to the hospital managed database; wherein said steps of rendering, updating and saving allow the hospital administrator to manage the hospital managed database.

8. A computer-enabled method for efficiently displaying an automatically generated hospital view of veterinary pharmaceutical and other animal-related product item records, each view item record being generated from item records of a products database, each products database item record comprising at least one unique item identifier field, a prescription required field, a price field, and a name field, and selectively modified by item records of a hospital managed database, each hospital managed database item record having multiple fields comprising at least a unique item identifier field, an exclude field, a price field and a name field, with at least one hospital managed database item record field optionally containing an overriding value, each hospital view item record having selectively displayed fields, comprising the steps of:
searching each item record of the products database for a corresponding item record in the hospital managed database and having a matching unique item identifier field;
storing in a hospital view at least part of each item record from the products database not having a corresponding item record in the hospital managed database;
not storing in the hospital view any part of each item record from the products database having a corresponding item record in the hospital managed database having the exclude field set to true; and
storing in the hospital view an item record having the exclude field set to false and containing at least one field defined by a corresponding field of a corresponding hospital managed database item record and each other field of the hospital view item record defined by a corresponding field of the corresponding products database item record.

9. The method of claim 8, wherein the steps of the method are applied to create a hospital view for each of a plurality of hospitals, each hospital having a unique hospital identifier, the unique hospital identifier being used to filter item record access in the hospital managed database so that the only item records available for use by a particular hospital user are those records corresponding to the unique hospital identifier.

10. The method of claim 8, wherein the steps of the method are applied to create an hospital view for a plurality of hospitals in a group, each group having a unique group identifier, the unique group identifier being used to filter item record access in the hospital managed database so that the only item records available for use by a particular group's users are those records corresponding to the unique group identifier.

11. The method of claim 8, wherein the steps of the method are used to create a list of product item records in the hospital view.

12. The method of claim 8, wherein the steps of the method are used to create a detailed item record in the hospital's view.

13. The method of claim 8, further comprising the step of using the output of the hospital view in a hospital client computer system wherein hospital staff may access only those products previously made available and selectively customized from the products and hospital managed databases for product selection in prescription creation and point-of-sale services.

14. A computer-enabled method for efficiently displaying an automatically generated user view of veterinary pharmaceutical and other animal-related product item records, each view item record being generated from item records of a products database, each products database item record comprising at least one unique item identifier field, a prescription required field, a price field, and a name field, and selectively modified by item records of a hospital managed database, each hospital managed database item record having multiple fields comprising at least a unique item identifier field, an exclude field, a price field and a name field, with at least one hospital managed database item record field optionally containing an overriding value, each user view item record having selectively displayed fields, comprising the steps of:
searching each item record of the products database having a prescription required field set to false for a corresponding item record in the hospital managed database having a matching unique item identifier field;
storing in a user view at least part of each item record from the products database having the prescription required field set to false and not having a corresponding item record in the hospital managed database;
not storing in the user view any part of any item record from the products database having a corresponding item record in the hospital managed database having the exclude field set to true; and
storing in the user view at least part of each item record from the products database having the prescription required field set to false, having the exclude field set to false and containing at least one field defined by a corresponding field of a corresponding hospital managed database item record and each other field of the user view item record defined by a corresponding field of the corresponding products database item record.

15. The method of claim 14, further comprising the step of using the output of the user view in a hospital e-commerce website for enabling hospital pet-owner customers to select and purchase only those products previously made available and selectively customized from the products and hospital managed databases.

16. The method of claim 14, wherein the steps of the method are used to create a list of product item records in the user view.

17. The method of claim 14, wherein the steps of the method are used to create a detailed item record in the user view.

* * * * *